(12) United States Patent
Babiak et al.

(10) Patent No.: US 9,931,385 B2
(45) Date of Patent: Apr. 3, 2018

(54) METHODS OF INHIBITING GONAD MATURATION

(71) Applicant: University of Nordland, Bodø (NO)

(72) Inventors: Igor Babiak, Tverlandet (NO); Reid Hole, Bodø (NO)

(73) Assignee: University of Nordland (NO)

( * ) Notice: Subject to any disclaimer, the term of this patent is extended or adjusted under 35 U.S.C. 154(b) by 0 days.

(21) Appl. No.: 14/383,564

(22) PCT Filed: Mar. 11, 2013

(86) PCT No.: PCT/GB2013/050592
§ 371 (c)(1),
(2) Date: Sep. 7, 2014

(87) PCT Pub. No.: WO2013/132274
PCT Pub. Date: Sep. 12, 2013

(65) Prior Publication Data
US 2015/0104474 A1 Apr. 16, 2015

(30) Foreign Application Priority Data

Mar. 9, 2012 (GB) .................................. 1204280.0

(51) Int. Cl.
*A61K 39/00* (2006.01)
*A61K 47/64* (2017.01)

(52) U.S. Cl.
CPC ........ *A61K 39/0005* (2013.01); *A61K 47/646* (2017.08); *A61K 2039/552* (2013.01); *A61K 2039/6031* (2013.01)

(58) Field of Classification Search
None
See application file for complete search history.

(56) References Cited

U.S. PATENT DOCUMENTS

| | | | |
|---|---|---|---|
| 4,798,885 A * | 1/1989 | Mason et al. ................ | 530/350 |
| 6,790,457 B1 * | 9/2004 | Brown ............... | A61K 39/0006 424/278.1 |
| 7,194,978 B2 | 3/2007 | Zohar .......................... | 119/217 |

FOREIGN PATENT DOCUMENTS

| | | |
|---|---|---|
| GB | 1204280.0 | 3/2012 |
| WO | WO 1979/000133 | 3/1979 |
| WO | WO 1989/003399 | 4/1989 |
| WO | WO 2000/037100 | 6/2000 |
| WO | WO 2007/031572 | 3/2007 |
| WO | WO 2012/106026 | 9/2012 |
| WO | PCT/GB2013/050592 | 3/2013 |
| WO | WO 2013/132274 | 9/2013 |

OTHER PUBLICATIONS

Adiga et al., Human Reproduction Update 1997, vol. 3, No. 4 pp. 325-334.*
Suri, Expert Opin. Biol. Ther. 2005; 5: 381-392.*
Naz, Biology of Reproduction, 2002; 67: 675-689.*
Presslauer et al., PLOS One DOI:10.1371/journal.pone.0114209; 30 pages total.*
Høvold et al., Veterinary Research 2014, 45:21.*
Hopp & Woods, Proc. Natl. Acad. Sci. USA, 1981; 78: 3824-3828.*
Li et al. (Biology of Reproduction, 2011; 84: 476-486.*
Park et al., Journal of Immunological Methods; 2012; 377: 15-22.*
McNalty et al., Biology of Reproduction, 2007; 76: 552-560.*
International Search Report and Written Opinion dated Sep. 11, 2013 for PCT Application No. PCT/GB2013/050592 filed on Mar. 11, 2013, which published as WO 2013/132274 on Sep. 12, 2013 (Igor Babiak, et al.—Inventors // University of Nordland—Applicant) (31 pages).
Berishvili G, et al. (2010) Insulin-like growth factor-3 (IGF-3) in male and female gonads of the tilapia: development and regulation of gene expression by growth hormone (GH) and 17alpha-ethinylestradiol (EE2). Gen Comp Endocrinol. 167(1):128-134.
Childs GV. (1990) Localization of gonadotropin-releasing hormone receptors. Methods Enzymol. 184:395-404.
Kirkpatrick JF, et al. (2011) Contraceptive vaccines for wildlife: a review. Am J Reprod Immunol. 66(1):40-50.
Nagasawa K, et al. (2010) Lymphocyte antigen 75 (Ly75/CD205) is a surface marker on mitotic germ cells in rainbow trout. Biol Reprod. 83(4):597-606.
Reinecke M. (2010) Insulin-like growth factors and fish reproduction. Biol Reprod. 82(4):656-661.
Sawatari E, et al. (2007) A novel transforming growth factor-beta superfamily member expressed in gonadal somatic cells enhances primordial germ cell and spermatogonial proliferation in rainbow trout (*Oncorhynchus mykiss*). Dev Biol. 301(1):266-275.
Ulker H, et al. (2005) Testicular development, ultrasonographic and histological appearance of the testis in ram lambs immunized against recombinant LHRH fusion proteins. Anim Reprod Sci. 86(3-4):205-219.
Ç akici, Özlem & Ü Ç üncü, Sema i Ş isag. Oocyte development in the Zebrafish, *Danio rerio* (Teleostei: Cyprinidae). EU J. Fish. Aquat. Sci. 24 (2007) 137-141.
Cross, Martin L. et al. Vaccinia virus as a vaccine delivery system for marsupial wildlife. Vaccine. 29 (2011) 4537-4543.
Delves, Peter J. et al. Antifertility vaccines. Trends Immunol. 23 (2002) 213-219.
Dziewulska, K & Domagala, J. Histology of salmonid testes during maturation. Reprod. Biol. 3 (2003) 47-61.
Ferro, Valerie A. & Garside, Deborah A. Reproductive component vaccine developments for contraceptive and non-contraceptive uses. Expert Opin. Ther. Pat. 21 (2011) 1473-1482.
Fujimoto, Takafumi et al. Sexual dimorphism of gonadal structure and gene expression in germ cell-deficient loach, a teleost fish. PNAS. 107 (2010) 17211-17216.

(Continued)

*Primary Examiner* — Christina M Borgeest
(74) *Attorney, Agent, or Firm* — Akerman LLP

(57) ABSTRACT

The present invention provides a method of inhibiting maturation of the gonads of a juvenile animal which comprises administering to said juvenile animal an immunologically active molecule (IAM) or a vector comprising nucleic acid encoding an immunologically active molecule, said IAM being specific for a target protein within the gonads and binding thereto or causing an immune response against that target protein, and thereby inhibiting maturation of the gonads, as well as molecules of use in such methods.

17 Claims, 7 Drawing Sheets

(56) References Cited

OTHER PUBLICATIONS

Figure 1:
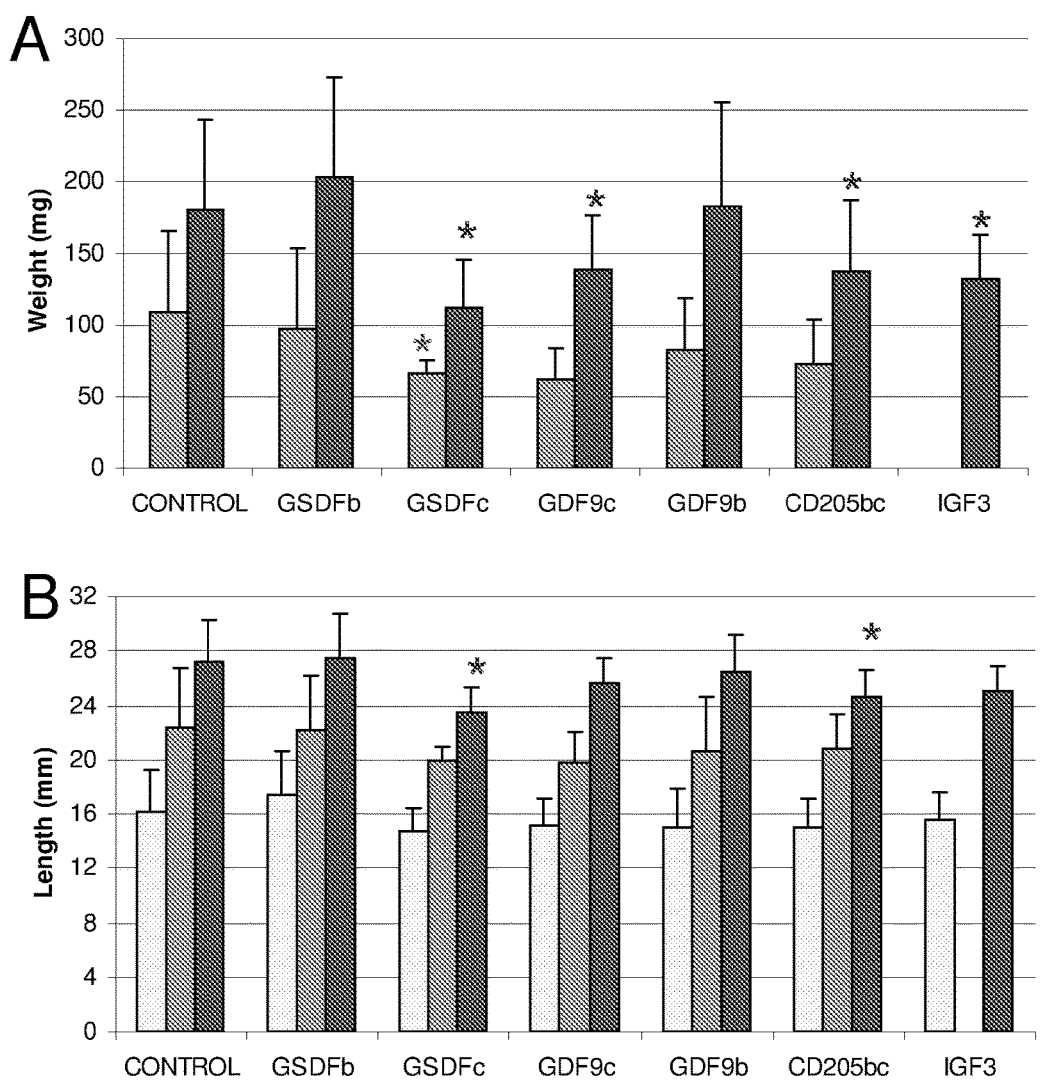

Gupta, Satish K. et al. Contraceptive Vaccines Based on the Zona Pellucida Glycoproteins for Dogs and Other Wildlife Population Management. Am. J. Reprod Immunol. 66 (2011) 51-62.

Hardy, C.M. et al. Biological control of vertebrate pests using virally vectored immunocontraception. J. Reprod. Immunol. 71 (2006) 102-111.

Juengel, Jennifer L. et al. Effects of Immunization Against Bone Morphogenetic Protein 15 and Growth Differentiation Factor 9 on Ovulation Rate, Fertilization, and Pregnancy in Ewes. Biol. Reprod. 70 (2004) 557-561.

Juengel, Jennifer L. et al. Effects of active immunization against growth differentiation factor 9 and/or bone morphogenetic protein 15 on ovarian function in cattle. Reprod. 138 (2009) 107-114.

Kerr, P.J. et al. Infertility in Female Rabbits (*Oryctolagus cuniculus*) Alloimmunized with the Rabbit Zona Pellucida Protein ZPB Either as a Purified Recombinant Recombinant Protein or Expressed by Recombinant Myxoma Virus Biol. Reprod. 61 (1999) 606-613.

Koç, Nazan Deniz et al. Ovary Maturation Stages and Histological Investigation of Ovary of the Zebrafish (*Danio rerio*). Braz. arch. biol. technol. 51 (2008) 513-522.

Laird, Lindsay M. et al. Field trials of a method of induction of autoimmune gonad rejection in Atlantic salmon (*Salmon solar* L.). Reprod. Nutr. Develop. 20 (1980) 1781-1788.

Levy, Julie K. Contraceptive Vaccines for the Humane Control of Community Cat Populations. Am. J. Reprod Immunol. 66 (2011) 63-70.

Li, Mingyou et al. Medaka vasa is required for migration but not survival of primordial germ cells. Mech. Dev. 126 (2009) 366-381.

Lo, S.C. et al. Current ZP3-based Immunocontraceptive Vaccine for Free Ranging Wild Pest Pertanika. J. Trop. Agric. Sci. 34 (2011) 1-16.

Maack, G. & Segner, H. Morphological development of the gonads in zebrafish. J. Fish Biol. 62 (2003) 895-906.

McLaughlin, E.A. & Aitken R.J. et al. Is there a role for immunocontraception? Mol. Cell. Endocrinol. 335 (2011) 78-88.

McNatty, Kenneth P. et al. The Effects of Immunizing Sheep with Different BMP15 or GDF9 Peptide Sequences on Ovarian Follicular Activity and Ovulation. Rate Biol. Reprod. 76 (2007) 552-560.

Moingeon, Philippe et al. Delivery technologies for human vaccines. Br. Med. Bull. 62 (2002) 29-44.

Naz, Rajesh K. Contraceptive Vaccines: Success, Status, and Future Perspective Am. J. Reprod. Immunol. 66 (2011) 2-4.

O'Leary, Sean et al. Immunization with Recombinant Murine Cytomegalovirus Expressing Murine Zona Pellucida 3 Causes Permanent Infertility in BALB/c Mice Due to Follicle Depletion and Ovulation Failure. Biol. Reprod. 79 (2008) 849-860.

O'Rand, M.G. et al. Reversible Immunocontraception in Male Monkeys Immunized with Eppin Science. 306 (2004) 1189-1190.

Slanchev, Krasimir. et al. Development without germ cells: The role of the germ line in zebrafish sex differentiation. PNAS. 102 (2005) 4074-4079.

Sreenivasan, Rajini et al. Transcriptomic Analyses Reveal Novel Genes with Sexually Dimorphic Expression in the Zebrafish Gonad and Brain. PLoS One 3 (2008) e1791.

Weidinger, Gilbert et al. *dead end*, a Novel Vertebrate Germ Plasm Component, Is Required for Zebrafish Primordial Germ Cell Migration and Survival. Curr. Biol. 13 (2003) 1429-1434.

White, Yvonne A.R. et al. A Transgenic Zebrafish Model of Targeted Oocyte Ablation and de novo Oogenesis. Dev. Dyn. 240 (2011) 1929-1937.

Xu, Hong Yan et al. Fish germ cells. Sci. China Life Sci. 53 (2010) 435-446.

Yamaha, E. et al. Primordial germ cell in teleost fish with special references to its specification and migration. J. Appl. Ichthyol. 26 (2010) 816-822.

Sawatari et al. A novel transforming growth factor-β superfamily member expressed in gonadal somatic cells enhances primordial germ cell and spermatogonail proliferation in rainbow trout (*Oncorhynchus mykiss*). Developmental Biology vol. 301, No. 1. (2007) 266-275.

\* cited by examiner

SEQUENCE LISTING

```
<160> NUMBER OF SEQ ID NOS: 29

<210> SEQ ID NO 1
<211> LENGTH: 16
<212> TYPE: PRT
<213> ORGANISM: Danio rerio

<400> SEQUENCE: 1

Phe Lys Thr Asp Gly Phe Glu Asp Asp Gly Asp Asp Ser Glu Glu Cys
1               5                   10                  15

<210> SEQ ID NO 2
<211> LENGTH: 16
<212> TYPE: PRT
<213> ORGANISM: Danio rerio

<400> SEQUENCE: 2

Leu Tyr Cys Ala Lys Ser Lys Lys Val Arg Arg Asp Val Pro Ala Cys
1               5                   10                  15

<210> SEQ ID NO 3
<211> LENGTH: 16
<212> TYPE: PRT
<213> ORGANISM: Danio rerio

<400> SEQUENCE: 3

Arg Val Gln Glu Gly Asp Pro Glu Glu Leu Asp Thr Thr Lys Ser Cys
1               5                   10                  15

<210> SEQ ID NO 4
<211> LENGTH: 16
<212> TYPE: PRT
<213> ORGANISM: Danio rerio

<400> SEQUENCE: 4

Ala Ser Lys Phe Leu Pro Arg Val Lys Asp Asp Lys Leu Arg Phe Cys
1               5                   10                  15

<210> SEQ ID NO 5
<211> LENGTH: 16
<212> TYPE: PRT
<213> ORGANISM: Danio rerio

<400> SEQUENCE: 5

Leu Tyr Cys Ala Lys Ser Lys Lys Val Arg Arg Asp Val Pro Ala Cys
1               5                   10                  15

<210> SEQ ID NO 6
<211> LENGTH: 15
<212> TYPE: PRT
<213> ORGANISM: Danio rerio

<400> SEQUENCE: 6

Glu Gly Ala Arg Ala Arg Cys Gly Arg Glu Leu Val Asp Asp Cys
1               5                   10                  15

<210> SEQ ID NO 7
<211> LENGTH: 16
```

<212> TYPE: PRT
<213> ORGANISM: Danio rerio

<400> SEQUENCE: 7

Arg Ser Gly Gly Pro Arg Ser Arg Gly Lys Gly Ile Val Asp Gln Cys
1               5                   10                  15

<210> SEQ ID NO 8
<211> LENGTH: 16
<212> TYPE: PRT
<213> ORGANISM: Danio rerio

<400> SEQUENCE: 8

Lys Ser Leu His Leu Pro Lys Glu Pro Ser Asn Ser Leu Ser Gln Cys
1               5                   10                  15

<210> SEQ ID NO 9
<211> LENGTH: 16
<212> TYPE: PRT
<213> ORGANISM: Danio rerio

<400> SEQUENCE: 9

Ser Leu Lys Asn Ser Ile His Ser Pro Pro Gly Asn Ser Ser Leu Cys
1               5                   10                  15

<210> SEQ ID NO 10
<211> LENGTH: 15
<212> TYPE: PRT
<213> ORGANISM: Danio rerio

<400> SEQUENCE: 10

Tyr Ser Phe Asp His Asn His Leu Ser Pro Phe Ser Leu Leu Cys
1               5                   10                  15

<210> SEQ ID NO 11
<211> LENGTH: 15
<212> TYPE: PRT
<213> ORGANISM: Danio rerio

<400> SEQUENCE: 11

Gln Ala His Lys Lys Asp Ile His Leu Leu Ile Asn Leu Thr Cys
1               5                   10                  15

<210> SEQ ID NO 12
<211> LENGTH: 16
<212> TYPE: PRT
<213> ORGANISM: Danio rerio

<400> SEQUENCE: 12

Asn Glu Asn Asp Thr Glu Ser Thr Val Arg Asp Val Tyr Lys Pro Cys
1               5                   10                  15

<210> SEQ ID NO 13
<211> LENGTH: 16
<212> TYPE: PRT
<213> ORGANISM: Danio rerio

<400> SEQUENCE: 13

Arg Arg Asn Pro Asn Thr Asn Asn Trp Glu Trp Ser Asp Gly Cys
1               5                   10                  15

<210> SEQ ID NO 14
<211> LENGTH: 19
<212> TYPE: DNA
<213> ORGANISM: Artificial Sequence

```
<220> FEATURE:
<223> OTHER INFORMATION: Primer

<400> SEQUENCE: 14
cgagctgtct tcccatcca                                                  19

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
tcaccaacgt agctgtcttt ctg                                             23

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ctggaggcca gctcaaacat                                                 20

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
atcaagaaga gtagtaccgc tagcattac                                       29

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
cacaacgagt tcaacattac cga                                             23

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
ccagaagatg cccagtgaca a                                               21

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
tggatgttgg cagcgtcac                                                  19
```

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gcactgctct cctgaaacct g                                            21

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
tcagagcaac aggtaatgag c                                            21

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
ctacagatgt ggcgaccaga ac                                           22

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
gaacgctcct gaatccacag ac                                           22

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
aatgactccc gcagatgctc                                              20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
agcctcctct gccagtgttg                                              20

<210> SEQ ID NO 27
<211> LENGTH: 23
<212> TYPE: DNA
<213> ORGANISM: Artificial Sequence
<220> FEATURE:
<223> OTHER INFORMATION: Primer

```
<400> SEQUENCE: 27
agcatcagaa gagtggtcag gta                                        23

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
tgctcctgtt cagtgtcaat cc                                         22

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
atgtctcaac catcgtcttc agt                                        23
```

METHODS OF INHIBITING GONAD MATURATION

This application is a national phase application of International Application No. PCT/GB2013/050592 filed Mar. 11, 2013, which claims priority to GB Application No. 1204280.0 filed Mar. 9, 2012, each of which is incorporated in its entirety by reference herein.

The present invention relates to methods of inhibiting maturation of the gonads of animals, in particular of fish. Such methods may reduce the fertility of the treated animals.

Rising human populations and over fishing of wild fish stocks means there is great pressure on commercial fish farming to increase production of fish for human consumption. Sexual maturation of farmed fish before they reach market size is one of the biggest problems raised by the producers. For example, in Atlantic cod, maturation occurs in the second year of life and results in loss of growth, condition and flesh quality. Also, fish escaping from production sites can genetically pollute natural populations and impact their fitness. After sexual maturation, energy is spent on gonadal growth instead of muscle growth. On the other hand, sterility increases the conversion of food energy to muscle and minimizes food energy diverted for development of the gonads. Induced sterility is therefore of great interest to the aquaculture industry.

The technique most used to produce sterile fish is induction of triploidy. However, this is a cumbersome procedure that must be individually developed for each species and does not always result in sterility and raises welfare concerns as it often results in developmental malformations.

Slanchev et al. in PNAS (2005) 102, 4074-4079 have described a possible alternative approach in which ablation of primordial germ cells (PGCs) results in development of sexually sterile individuals. In this study, embryos were injected with antisense molecules directed against a transcript of dead end, a gene important for the survival of PGCs. While PGC ablation through genetic knockdown of dead end transcripts has been demonstrated in several fish species, the technique uses expensive morpholino oligonucleotides which are microinjected manually in every single embryo at around the 1-cell stage of development, which means it cannot be easily translated into a mass-scale method.

In a further approach, targeted cell ablation has been demonstrated as effective technology to induce infertility in zebrafish gonads. This technology was developed using transgenic lines expressing nitroreductase enzyme (Ntr) under control of tissue-specific promoters; upon delivery of the prodrug metronidazole (Met), Ntr converted Met into cytotoxins causing cell death (White et al. (2011) Developmental Dynamics 240: 1929-1937). Although effective, a potential technology using such a mechanism in the human food-chain would face perception issues because of GMO technology and human health considerations.

A further approach for inducing sterility in farmed fish is described in U.S. Pat. No. 7,194,978. Here gonadal development is disrupted by interfering with the gonadotropin-releasing hormone system; this is achieved by immersing larval fish in GABA or a GABA agonist which results in altered gonadotropin-releasing hormone gene expression during early development which in turn inhibits gonadal development. However, this method has not been taken up by the aquaculture industry.

As an alternative to the above strategies, the present inventors propose a method of impairing gonad development via immune mechanisms. Immunocontraceptive vaccines have been shown to be effective in many species (Kirkpatrick et al., American Journal of Reproductive Immunology 66 [2011] 40-50) but the process is typically reversible and sexually mature animals are targeted in order to affect fertilization ability of mature gametes. In contrast, by targeting gonad development in juveniles, loss of fertility may be irreversible. Moreover, while these prior art vaccines may serve the purpose of restricting population growth, they are not suitable for aquaculture as they do not prevent gonadal maturation and the associated effects on flesh quality.

Thus, in a first aspect, the present invention provides:
a method of inhibiting maturation of the gonads of a juvenile animal which comprises administering to said juvenile animal an immunologically active molecule (IAM) or a vector comprising nucleic acid encoding an immunologically active molecule, said molecule binding to, or stimulating production of antibodies which bind to, a target protein in the gonads. The administration can result in irreversible infertility in said juvenile animal; successful administration will result in reduced fertility in said animal, such reductions typically being irreversible.

Without wishing to be bound by theory, it is believed that administration (i.e. vaccination) will induce an immune response, which may involve both B cells and T cells. B cells secrete antibodies which bind to the target protein and interfere with its function; T cells are able to cause cell ablation directly, e.g. through binding to target protein on the cell surface.

Thus, alternatively viewed, the present invention provides a method of inhibiting maturation of the gonads of a juvenile animal which comprises administering to said juvenile animal an immunologically active molecule (IAM) or a vector comprising nucleic acid encoding an immunologically active molecule, said IAM being specific for a target protein within the gonads and binding thereto or causing an immune response against that target protein, and thereby inhibiting maturation of the gonads.

Preferably, the immune response includes activation of B cells and production of antibodies which bind to the target protein in the gonads and/or stimulation of T cells, in particular T cell binding to a target protein in the gonads. Specific T cell binding to target protein may be through T Cell Receptors on the surface of the T cell, such binding may cause cell death. Activation of both cell types is shown in the Examples by upregulation of marker genes.

The target animals are juveniles, i.e. they are young forms of the species which are not yet sexually mature but phenotypically they resemble an adult form. In salmonids, the juvenile stage is termed the parr and smolt stages. In a juvenile, as compared to an adult, the gametes in the gonads are not mature, therefore cannot be released for reproduction. Thus a juvenile may have some or all of the physical structure of a gonad but the gonad is not mature in that the gametes are not mature or able to take part in natural reproduction. In general, while the development of gonads can start as early as the embryo stage, the final morphological organisation of the gonad comes at a juvenile stage.

As well as reproductive incapacity through lack of mature gametes, the skilled man is aware of techniques to assess juvenile status through study of the gonads, for example as described in zebrafish by Maack et al. (2003) Journal of Fish Biology 62, 895-906 and in salmonids by Dziewulska et al. (2003) Reproductive Biology Vol. 3, No. 1, 47-61. Thus gonad immaturity can be determined by histological examination, inter alia through examination of the gametes. The morphology of gametes changes as they mature; for example, a fully mature oocyte is sometimes classified as stage V. In the testes, mature gametes are morphologically distinctive spermatoza.

As a general classification in lower and many higher vertebrates, the developmental stages are (1) haploid gametes, (2) embryo, (3) larva, (4) juvenile and (5) adult. Thus, an embryo or larva is not a "juvenile".

The targeting of juveniles is key to the present invention and can be contrasted with approaches to control fertility which are based on administration to the broodstock, i.e. sexually mature animals, or to the embryo. Depending on the route of administration chosen, animals other than juveniles may be exposed to and/or receive an IAM but such animals are not the target animals of the methods of the present invention. Preferably only juvenile animals within an animal population are administered to.

By targeting juveniles and gonad development, irreversible infertility in the target animals may be achieved. This can be contrasted with many immunocontraceptives which are administered to sexually mature animals and have a temporary effect on fertility. By 'irreversible' infertility is meant that, after successful administration, it is not necessary to continue administrations during the life of the animal (although the initial treatment may involve multiple administrations) to maintain infertility. Because the natural maturation of the gonads has been impaired, the gonads are effectively permanently retarded and may either be suspended in a juvenile state or even experience atrophy or damage. Such changes can result in irreversible infertility.

Nevertheless, it will be appreciated that in any treated population, a proportion of animals may retain (or revert to) some degree of reproductive capacity. "Infertility" is thus understood on this basis. While individual animals may be treated, a successful treatment regimen will generally be judged at the population level. Thus the methods of the invention will typically result in a reduction in reproductive performance of a population of at least 50%, preferably at least 60%, more preferably at least 70% or even at least 80%. These changes in the fertilization capacity of the population as a whole will reflect a variety of individual responses, e.g. from complete retardation of the gonads to some or modest retardation and reduction in reproductive capacity. Preferably no more than 40%, more preferably no more than 20% or even 10% of animals in the treated population will exhibit normal fertility after treatment. Preferably some of the treated animals will be sterile, i.e. completely infertile, e.g. at least 40%, preferably at least 50 or 60% of the animals.

Thus, in a further aspect, the present invention provides a method of inhibiting maturation of the gonads in a population of juvenile animals, which comprises administering to said population an immunologically active molecule (IAM) or a vector comprising nucleic acid encoding an immunologically active molecule, said molecule binding to, or stimulating production of antibodies which bind to, a target protein in the gonads. The administration preferably results in irreversibly reduced reproductive capability in said population. Reproductive performance or capability can be measured against a similar untreated population and/or against historical norms.

Alternatively viewed, the invention provides a method of inhibiting maturation of the gonads in a population of juvenile animals, which comprises administering to said population an immunologically active molecule (IAM) or a vector comprising nucleic acid encoding an immunologically active molecule, said IAM being specific for a target protein within the gonads and binding thereto or causing an immune response against that target protein, and thereby inhibiting maturation of the gonads of the animals in said population.

The methods of the present invention can lead to reduced fertility, preferably irreversibly reduced fertility. Thus, alternatively viewed, the present invention provides a method of reducing fertility in a juvenile animal or a population of juvenile animals which comprises administering to said animal or population of animals an immunologically active molecule (IAM) or a vector comprising nucleic acid encoding an immunologically active molecule, said IAM being specific for a target protein within the gonads and binding thereto or causing an immune response against that target protein, and thereby inhibiting maturation of the gonads of said animal(s).

Preferably the methods of the invention improve yields in the farming of livestock, in particular in aquaculture, as a result of enhanced muscle growth due to reduced energy expenditure on gonad growth. Thus, alternatively viewed, the present invention provides a method of enhancing muscle growth in a juvenile animal or a population of juvenile animals, which comprises administering to said animal or population of animals an immunologically active molecule (IAM) or a vector comprising nucleic acid encoding an immunologically active molecule, said IAM being specific for a target protein within the gonads and binding thereto or causing an immune response against that target protein, and thereby inhibiting maturation of the gonads of said animal(s).

Enhanced muscle growth can be determined relative to a control group and is typically a long term benefit of the methods of the present invention. Overall weight of an individual animal may be less, but given the significant contribution to weight of the gonads in some animals, in particular in fish, the proportion of muscle, of edible, high value flesh may still be increased.

According to the methods of the present invention, maturation of the gonads is inhibited. Typically, there is significant impairment of normal gonadal morphology (as well as function) resulting in reduced gonad mass as compared to a normal adult. The animals preferably develop to adult size in other respects and muscle mass growth will preferably proceed as in normal development, or even in a superior fashion. As discussed above in the context of confirming juvenile status, techniques exist to analyse the gonads and determine morphological features which can confirm inhibited maturation. Measurement of hormone levels would provide an alternative method to confirm successful inhibition of gonad maturation. A lack of, or reduction in, releasable gametes is a key indicator of inhibited maturation of the gonads. If gonadal maturation is completely prevented, gametes cannot be released therefrom for reproduction, despite the fact the animal is of a sufficient age in weeks, months, years (as appropriate) to be sexually mature. As discussed above in the context of infertility, it will be appreciated that individual animals may experience more or less inhibition of gonadal maturation and success will typically be judged at the population level. Preferably most (e.g. at least 60, or 70%) of the treated animals will exhibit some inhibition and some will exhibit complete inhibition, e.g. at least 40%, preferably at least 50 or 60% of the animals.

The target protein is found in the gonads and is typically specific to the gonads, in that it is expressed only or predominantly in the gonad. The target protein typically has a structural or regulatory role in development or maintenance of the gonad, either being a germline protein or a protein of somatic cells, e.g. that are supportive of the gametes in the overall gonad structure. Supporting somatic cells include, but are not restricted to, Sertoli and Leydig cells in the testes and ovarian follicle and granulosa cells in the ovaries.

The target protein is a known protein which has been selected for the role it plays or may play in the structure or function of the gonad. The IAM is designed to be reactive to this specific target protein, e.g. to bind thereto, to generate antibodies reactive to this target protein and/or to illicit a T cell response which is specific to this target protein. Thus the IAM is specific for a predetermined target protein. Methods of the invention may involve selection of a target protein and the design or selection of an IAM specific for that target protein.

Preferably the IAM is an antigenic peptide, preferably a peptide generated by recombinant technology or by de novo peptide synthesis. In which case the sequence of the peptide is predetermined and based on the amino acid sequence of the target protein. Analysis can be done of the native sequence and antigenicity predicted. The antigenic peptide which is administered may be a heteroantigen, i.e. its sequence differs from the equivalent region of the native sequence in order to enhance antigenicity. The antigenic peptides are conveniently 10-40 amino acids, preferably 10-25 amino acids, more preferably 12-20 amino acids in length. The antigenic peptides may be conjugated to a carrier protein, as described further herein. The peptide is typically a fragment of the target protein or, in the case of a heteroantigen, corresponds to a short antigenic region of the target protein. Thus the IAM is preferably not the whole target protein and is a synthetic and not a naturally occurring molecule.

While it is possible that more than one IAM, e.g. more than one antigen (to the same or different target proteins), may be administered, in each case the IAM will have a specific target protein that has been selected and used in the design, selection and/or production of the IAM. Thus the reactivity, e.g. antigenicity, of the formulation which is administered to the animals is controlled and, absent any side effects caused by unexpected crossreactivity, predictable.

It is a surprising benefit of the present invention that targeting a single protein within the gonads is able to cause fundamental impairment of gonad maturation and thereby function and fertility.

Gonadal transcriptome databases exist, e.g. for zebrafish described by Sreenivasan et al PLOS One 6(4), e 18181. Suitable targets can be identified from such databases and the literature. The principle being that gonadal development is disrupted through immunization against key proteins involved in gonadal development.

Suitable target proteins include structural cell surface proteins, cell surface receptors, cell interaction proteins, signalling proteins and vitamin carrier proteins. Cell surface receptors are particularly preferred and, without wishing to be bound by theory, it is believed that both B and T cell mediated effects impair gonad maturation for this category of target protein. Signalling proteins will, in contrast, tend to rely on antibodies secreted by B cells, whereas T-cell responses are believed to play the most significant role in gonad impairment when the target protein is a structural surface protein. Examples of targets in each category are given below. Signalling ligands are a further class of preferred target proteins.

Structural Surface Proteins:
Zona pellucida C—A glycoprotein localized in oocytes. It plays a role both in oocyte structure and in fertilization. There is evidence of both a prevention of fertilization, and ovarian pathology when immunized against.
A-kinase anchoring protein 4 (AKAP4)—This is a structural protein associated with the sperm flagellum. It is well conserved in vertebrates and is expressed in zebrafish testis.
Outer dense fiber of sperm tail gene 3 (odf3)—In humans, the protein is a main component in the structure of the sperm tail. The gene is strongly up-regulated in zebrafish testis.

Cell Surface Receptors:
IB bone morphogenetic protein receptor (Alk6b)—This is a receptor for BMP signalling which plays an important role in germ cell formation, development, and maturation. It is expressed in germ cells, spermatocytes, and stage I and II oocytes. Zebrafish mutations prevent germ cell differentiation, resulting in germ cell tumors.
Vitellogenin receptors (VtgR)—Vitellogenin (Vtg) is essential to oocyte development. VtgR(s) are lipoprotein receptors expressed by oocytes to facilitate uptake of Vtg, as well as other important nutrients such as riboflavin, into the cell.
Mannose 6-Phosphate receptor (M6PR)—This receptor is found on the surface of spermatocytes, spermatids, and sertoli cells. It is thought to play a role of mediator in germ cell—sertoli cell interactions.
Lymphocyte antigen 75 (CD205/Ly75)—This protein is a receptor belonging to the macrophage mannose receptor (MMR) family. In mammals its role is characterized by antigen uptake, processing, and presentation associated with dendritic cells. In fishes, CD205 is expressed on the surface of germ cells and early stage spermatogonia and oocytes.
Rhamnose binding lectins—(STL1/STL2)—These are found on the surface of rainbow trout oocytes. Their exact physiological function unknown. Their transcripts were shown to be upregulated in zebrafish ovaries.

Cell Interaction Proteins:
Connexin43 (Cx43)—Connexins are transmembrane proteins which assemble to form gap junctions between cells. Cx43 is the predominant connexin found in the testis and ovary.
Testis-specific protein 1 (Tpx-1/CRISP2)—Testis specific adhesion molecule important for the interaction of Sertoli and spermatogenic cells.
Sperm adhesion molecule 1 (SPAM1/PH-20)—Sperm cell surface receptor having hyaluronidase (enzymatic) activity. It enables sperm to penetrate through the hyaluronic acid-rich cumulus cell layer surrounding the oocyte (in mammals). It is involved in sperm-zona pellucida adhesion.
Sperm associated antigen (1→8) (SPAG8)—Sperm cell surface receptor. It is located in acrosomal region of spermatozoa (similarly as PH-20), plays a role in spermatogenesis (in mammals).

Signalling Ligands:
Insulin-like growth factor 3 (IGF3)—IGF3 is a gonad-specific insulin-like growth factor sub-type found only in teleost fishes. It has been linked to ovarian functions, specifically oocyte maturation. Other studies have shown it is involved in regulating gonad steroidogenesis.
Growth differentiation factor 9 (GDF9)—GDF9 is an oocyte specific growth factor of the transforming growth factor β family. It is strongly expressed in oocytes during the primary growth stage.
Gonadal soma-derived growth factor (GSDF)—GSDF is a growth factor expressed by both granulosa and Sertoli cells. It plays an important role in germ cell proliferation.

Anti-Müllerian hormone (AMH)—AMH is a member of the transforming growth factor β family of growth and differentiation factors. It plays an important role in male sex determination.

Inhibin α subunit (inhα)—Inhα is a member of the transforming growth factor β family of growth and differentiation factors. It is expressed by granulosa cells during primary oocyte growth, folliculogenesis and vitellogenesis.

Bone morphogenetic protein 15 (BMP15)—BMP15 is a member of the transforming growth factor β family of growth and differentiation factors. Its signalling is critical for normal fertility in female mammals.

Vitamin Carrier Proteins:

Riboflavin carrier protein (RCP)—Riboflavin (B2) is a vitamin critical to embryo development. Immunization for RCP, effectively preventing vitamin deposition, has been effective as an immunocontraceptive in mammals.

Many of the above targets are specific to fish but equivalent proteins exist in the gonads of other species, e.g. in mammals and these represent further suitable targets.

The methods of the present invention make use of the ability of antibodies or other antigen binding molecules to bind to a target protein and interfere with its normal function, in the present case leading to inhibition of gonad maturation. Inhibition of gonad maturation can also be caused by other autoimmune responses to introduced antigen, for example involving stimulation of cytotoxic T cells. The term 'immunologically active molecule' (IAM) includes both antibodies and antigens and antibody fragments such as Fab or scFv fragments and engineered variants such as diabodies, triabodies, minibodies and single-domain antibodies. Recent advances in the generation of molecular libraries and affinity screening has meant that identification of binding proteins with specific affinity for a given antigen target is relatively straightforward. Antibodies may be monoclonal or polyclonal.

The administered IAM may bind to the target protein or stimulate production of antibodies in the juvenile animal which bind to the target protein or stimulate production of cytotoxic cells, such as T cells, which bind to the target protein. Antigen used to prompt generation of antibodies in the animal may be different from that of the target species to enhance the immune response (i.e. a heteroantigen), including Ab production, but still similar enough so that the antibodies produced will bind to the target protein in the juvenile animal of interest (e.g. Atlantic salmon for zebrafish and vice versa). This is the classic vaccine model. As described in the Examples, methods for selection of antigenic peptides from within a target protein sequence are known in the art (e.g. Hopp and Woods (1981) Proc. Nac. Acad. Sci 78, 3824-3828).

Alternatively, antibodies to the target protein may be generated in a host animal and administered to the juvenile animal. This has the benefit of immediate impact as there is no delay while the animal's immune system generates antibodies to an introduced antigen and the effective concentration can be regulated. In other circumstances administration of antigen may be preferred as they are typically cheaper to produce and can be readily administered into the body cavity and illicit a wider autoimmune response.

The Experimental section herein provides detail on protocols for generation of IAMs. In addition, there are some commercially available antibodies to many of the target proteins discussed above, in particular to Zpc. Suitable antigen based vaccines are described in Kirkpatrick (supra). SpayVac is a further antigen based vaccine to Zp. Successful reversible immunocontraception has also been shown by targeting eppin in primates (Rand et al. [2004] Science, 306, 5699, pp 1189-1190), which suggests a role for such a vaccine in treating juveniles according to the methods of the present invention. Likewise, WO 00/37100 teaches the use of a teleost homolog of zona pellucida as an immunocontraceptive vaccine for sexually mature fish and birds.

Preferred antigenic peptides (IAMs) are identified in Tables 1 and 2 and these molecules and larger peptides incorporating them (but not the full length target proteins) and these peptides conjugated to carrier proteins constitute further aspects of the present invention. The peptides of Table 2 are preferred in these embodiments.

In the vaccine approach an adjuvant is preferably co-administered, e.g. Freund's complete adjuvant, Freund's incomplete adjuvant, MF89, Gerbu, Titermax, or Montanide.

The IAM, e.g. purified antibodies or antisera or antigen may be administered in any suitable carrier or formulation, for example in a simple buffer such as PBS or in tailored delivery vehicles such as liposomes or ISCOMs (Immune stimulating complexes). Antigens may conveniently be delivered in microspheres or virus-like particles or bacterial ghosts or live bacterial or viral vectors. Kerr et al in Biology of Reproduction (1999) 61, 603-613 describe techniques for successful delivery of antigen or a virus expressing an antigen to generate antibodies against a gonadal protein, albeit in adult rabbits. However, preferably the IAM is not administered as part of a bacterial or viral vector, particularly preferably not in a live vector.

Administered antigens may be made up of single epitopes, possibly of no more than 10, or even fewer amino acids, preferably 10 to 20 amino acids. Conveniently the Invitrogen Peptide Select Tool may be used for designing the antigen. Such small antigens may conveniently be coupled to a carrier protein, such as maleimide-activated KLH. Such conjugations are conveniently performed using kits, e.g. as provided by Sigma-Aldrich.

As an alternative to direct administration of an IAM, it may be preferred to deliver a nucleic acid molecule encoding an IAM, particularly DNA vaccines encoding an antigen, e.g. a bacterial, viral or plasmid vector. Such vectors are well known to the person skilled in the art. Suitable viral vaccines include those utilising ectromelia, poxviruses such as myxoma or vaccinia viruses. Hardy et al. (2006) Journal of Reproductive Immunology 71, 102-111 describes viral vectors for immunocontraception and such molecules and techniques apply, mutatis mutandis, to the methods of the present invention.

Administration may be any convenient means for delivery of a vaccine or, more generally, for delivery of biological pharmaceuticals. Administration may be via a mucosal surface, in particular by oral administration, or via a parenteral route, e.g. by a subcutaneous, intraperitoneal, intramuscular, intravenous or intradermal route. Injection and oral methods of administration are preferred routes. In fish administration is preferably by injection but may be oral, in particular with a virus based vaccine, more preferably by intraperitoneal injection, for example into the abdominal cavity, e.g. posterior to the pelvic girdle, or by intramuscular injection, e.g. below the dorsal fin; intramuscular administration is particularly suitable for delivery of antibodies.

Administration is preferably in a single dose but it may be in multiple doses, (booster doses), such as repeated once, or more times (e.g. 2-5 times).

Administration may be in animal feed and animal feed formulations comprising one or more feedstuffs and an IAM or nucleic acid encoding an IAM as defined herein is a further aspect of the present invention. Preferred feed formulations are fish feeds. Typically feeds will comprise sources of carbohydrate, protein, fibre and/or lipid, optionally together with micronutrients. It may be advantageous to add the molecules and compositions of the invention to the water in tanks housing juvenile fish.

Administration of antibody or antigen will typically involve delivery of 0.2-10 µl e.g. 1-5 µl, of formulation per 0.1 g of body weight.

The formulation comprising the IAM or nucleic acid encoding the IAM will typically be in a solution, suspension or emulsion. Suitable diluents or carriers are well known in the art.

The animal which is treated according to the present invention is a non-human animal, typically an animal in the human food chain, i.e. which are consumed by humans and farmed as such. Preferred animals are chordates and may be mammalian or non-mammalian. Particularly preferred are fish, especially Teleostei, in particular farmed fish. Farmed animals, livestock (terrestrial or aquatic), as well as domestic or pest animals are suitable targets. Species of particular interest include Atlantic salmon (*Salmo salar*), rainbow trout (*Oncorhynchus mykiss*), Atlantic cod (*Gadus morhua*), and Atlantic halibut (*Hippoglossus hippoglossus*). Experimental species such as zebrafish are also of interest.

Both male and female animals can be targeted according to the present invention, sometimes just one or the other as target proteins may be sex specific but some target proteins will not be sex specific e.g. GSDF (gonadal soma-derived factor) and IAMs which are not sex specific are particularly preferred according to the present invention. It is a further surprising advantage of the present invention that a single IAM or a single target protein can be used to inhibit gonad maturation in both males and females. It may be preferred to target females.

The present invention provides an immunologically active molecule (IAM) or a vector comprising nucleic acid encoding an immunologically active molecule, said molecule binding to, or stimulating production of antibodies which bind to, a target protein in the gonads, for use in inhibiting maturation of the gonads of a juvenile animal.

In a further aspect, the present invention provides an immunologically active molecule (IAM) or a vector comprising nucleic acid encoding an immunologically active molecule, said IAM being specific for a target protein within the gonads and capable of binding thereto or causing an immune response against that target protein for use in inhibiting maturation of the gonads of a juvenile animal.

In yet a further aspect, the present invention provides an immunologically active molecule (IAM) or a vector comprising nucleic acid encoding an immunologically active molecule, said molecule binding to, or stimulating production of antibodies which bind to, a target protein in the gonads, for use in irreversibly reducing fertility in a juvenile animal.

In yet a further aspect, the present invention provides an immunologically active molecule (IAM) or a vector comprising nucleic acid encoding an immunologically active molecule, said IAM being specific for a target protein within the gonads and capable of binding thereto or causing an immune response against that target protein for use in irreversibly reducing fertility in a juvenile animal.

Preferred aspects of the methods described above apply equally to these uses. The uses also apply, mutatis mutandis, to methods applied to populations of juvenile animals. Alternative uses include to reduce fertility and to enhance muscle growth.

In further aspects, the present invention provides the use of IAMs as defined herein in the manufacture of an agent for inhibiting maturation of the gonads of a juvenile animal, for (irreversibly) reducing fertility in a juvenile animal or enhancing muscle growth in a juvenile animal.

The above defined IAMs and nucleic acid molecules encoding them constitute further aspects of the present invention, as do compositions, in particular pharmaceutical or feed formulations, comprising them and uses of them. Preferred pharmaceutical formulations are vaccine formulations, which optionally also contain an adjuvant.

In certain embodiments target proteins in the male gonad are preferred, or if female target proteins are selected they do not include the zona pellucida/radiata, in particular ZP-3 (or equivalent proteins thereto) are not included.

The invention will now be further described in the following, non-limiting, experimental section and Examples and with reference to the following Figures, in which:

FIG. 1 shows the distribution of average weight (A) and length (B) of juvenile zebrafish immunized with the tested antigens. In Figure (A), the day 15 data are presented in the left-hand bars, the day 30 data in the right-hand bars. In Figure (B), the day 0 data are presented in the left-hand bars, the day 15 data in the middle bars and the day 30 data in the right-hand bars. Asterisks mark variants differing significantly from control group (p<0.05). T-bars show standard deviation.

Figure 2:
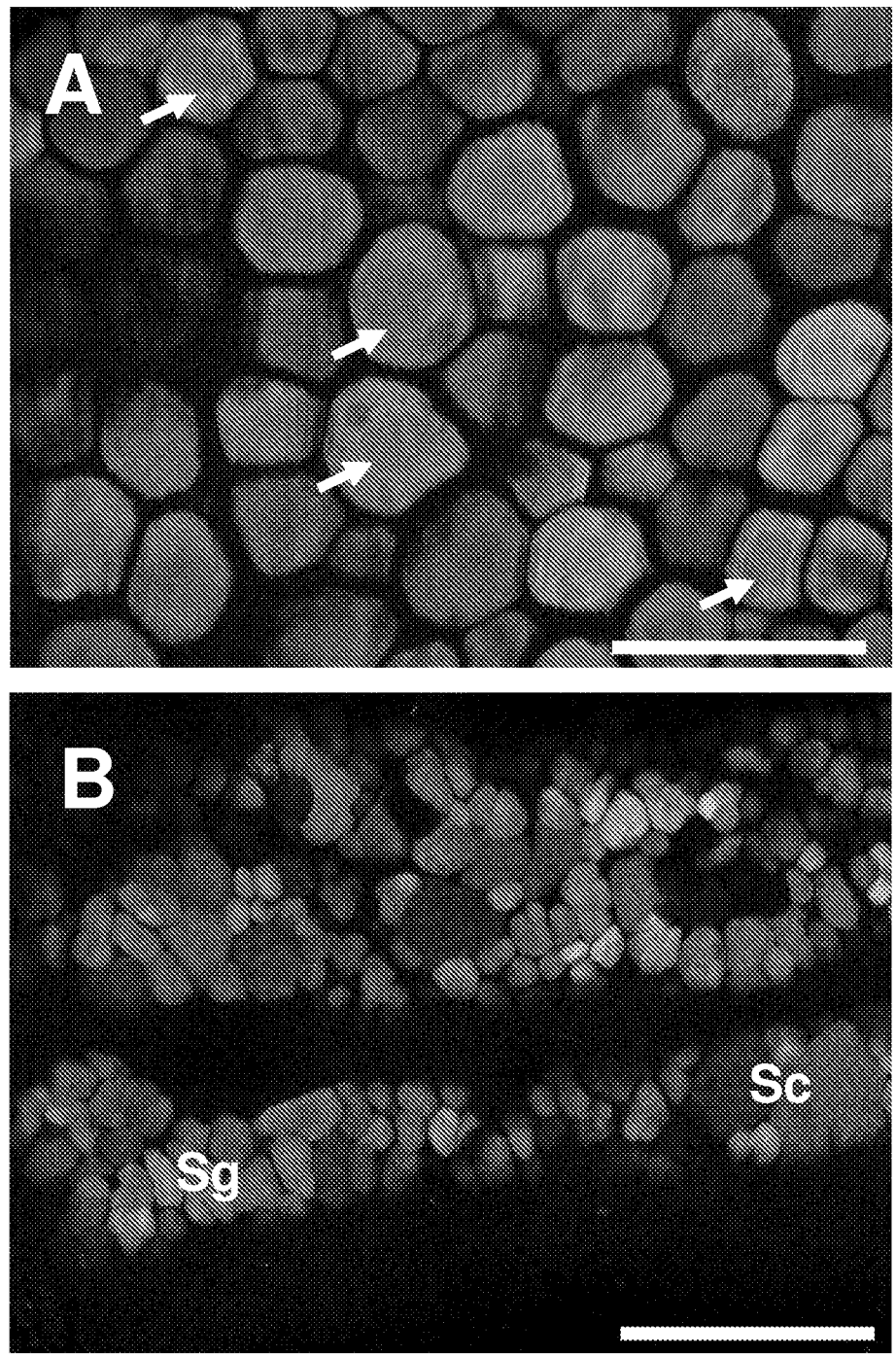

FIG. 2 shows the GFP signal in ovary (A) and testis (B) of tg(vas::egfp) zebrafish gonad under epifluorescent light. In ovary, stage IB oocyctes are visible. The GFP protein is distributed transiently in the cytoplasm, with particularly strong signal visible around the nucleus (arrows). In testis, strong signal is observed in spermatogonia (Sg) only, whereas signal in spermatocytes (Sc) is clearly weaker. Scale bar indicates 100 µm.

Figure 3:
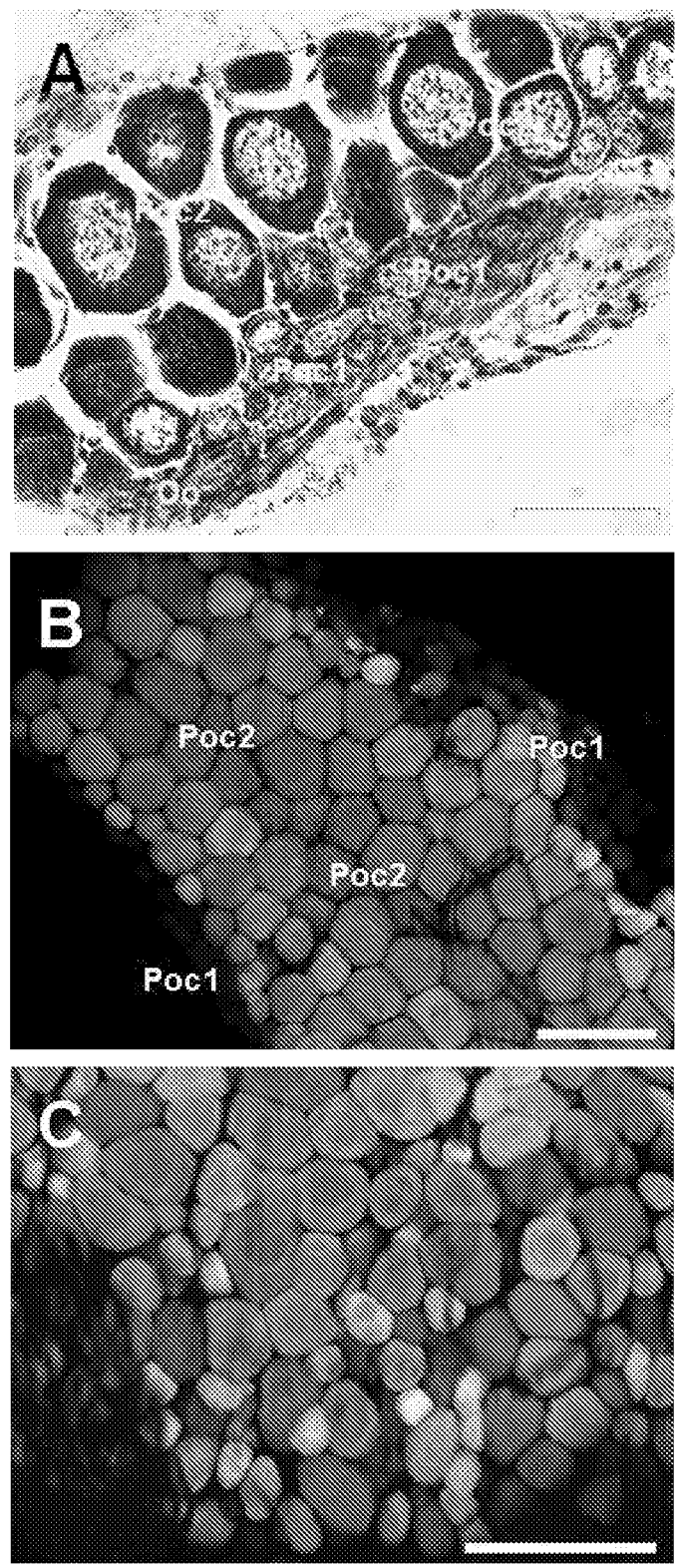

FIG. 3 shows the representation of previtellogenic ovary development (stage IB) of zebrafish at 15 days post-treatment. In a normal developmental pattern, more advanced stages are inwards the ovary, whereas earlier stages are predominantly clustered at margins. FIG. 3A shows the histological section of a control fish 36.8 mg, 17.2 mm. FIG. 3B shows an ApoTome image of a control fish (57.9 mg, 20.0 mm). FIG. 3C shows an ApoTome image of ovary of anti-CD205 treated fish (69.4 mg, 21.0 mm). FIG. 3C shows that the various developmental stages are mixed. Poc1—Primary oocytes at stage 1, Poc2—primary oocytes at stage 2, Oo—oogonia. Scale bars represent 50 µm (FIG. 3A) and 100 µm (FIGS. 3B and 3C).

Figure 4:
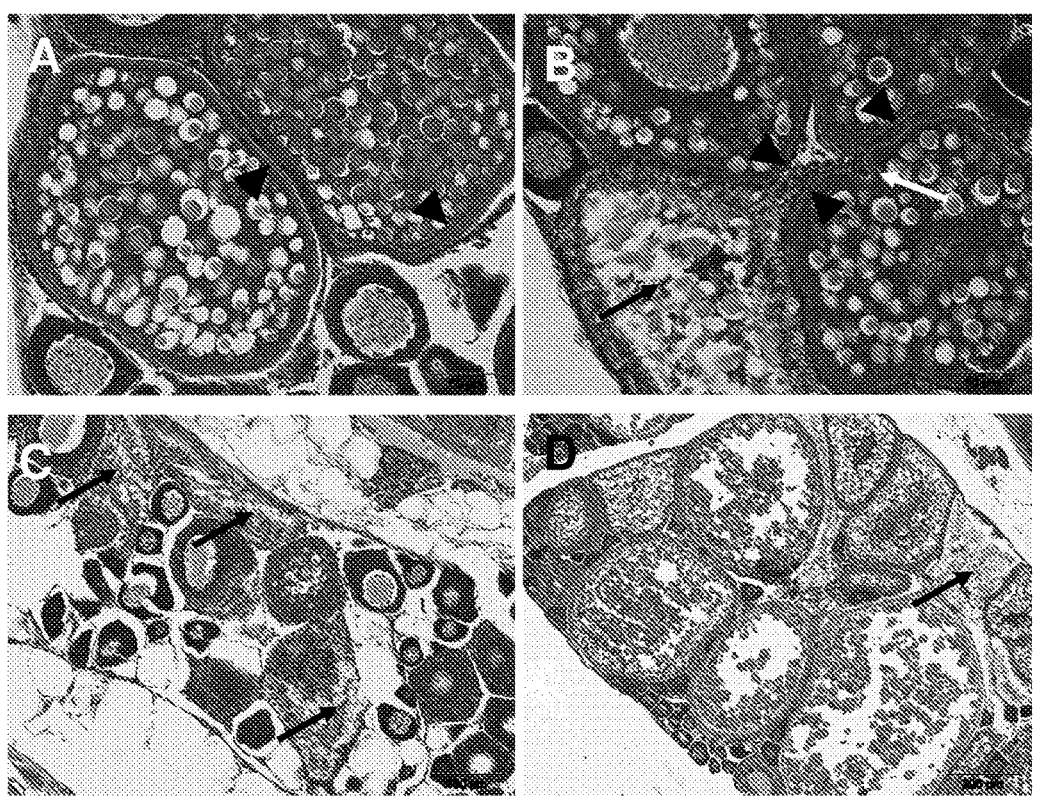

FIG. 4 shows atresia and atrophy in previtellogenic and vitellogenic oocytes (stages II-IV) in treated zebrafish at 30 days post-treatment. FIG. 4A shows normal development in control fish (216 mg, 29.9 mm), cortical alveolus stage (stage III): the two follicles have thick zona radiata. FIG. 4B shows ovary of anti-CD205 treated fish (241 mg, 30.5 mm), the same stage of development; zona radiata is thinner, invagination of zona radiata indicates atresia, and atrophic follicles are visible. FIG. 4C shows atrophic follicles in ovary of anti-CD205 treated fish (222 mg, 30.4 mm) at stage II of ovary development. FIG. 4D shows previtellogenic and vitellogenic oocytes in anti-GSDFb treated fish (326 mg and 31.9 mm) with atrophy. Atrophic follicles and atretic invagination of zona radiata are indicated with black and white arrows, respectively. Arrowheads point to zona radiata.

Figure 5:
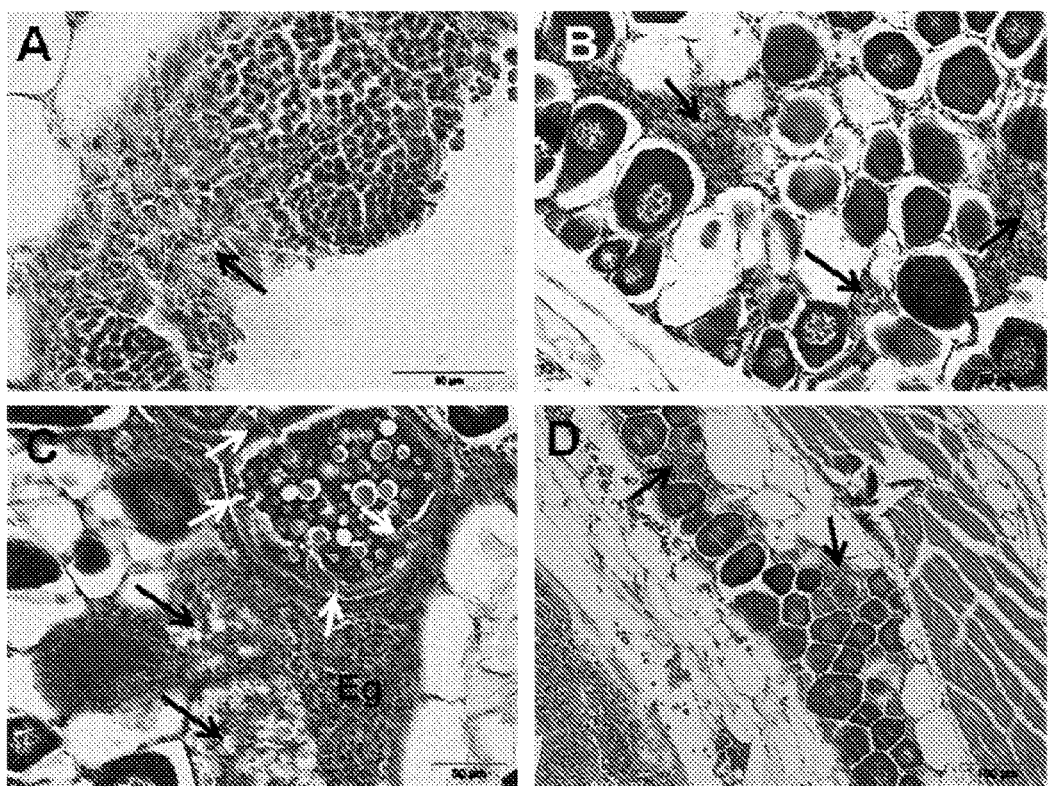

FIG. 5 shows inflammation in developing gonads of anti-CD205 treated zebrafish. FIG. 5A shows infiltration of peritoneal cells (arrow) into testis, 15 days post-treatment (fish size 165 mg, 26.6 mm). FIG. 5B shows infiltration of the eosinophilic granulocytes and other peritoneal cells into gonadal stroma (arrows) of stage II ovary (fish size 81 mg, 22.9 mm). FIG. 5C shows cortical alveolus stage oocytes (fish size 241 mg, 30.5 mm): invaginations in zona radiata (white arrows) indicate atretic processes; follicles in advanced atrophy (black arrows) are also visible along with infiltration of eosinophilic granulocytes (Eg). (D) Infiltration of the eosinophilic granulocytes (arrows) into stage II ovary (fish size 128 mg, 25.1 mm). FIGS. 5B to 5D are 30 days post treatment.

Figure 6:
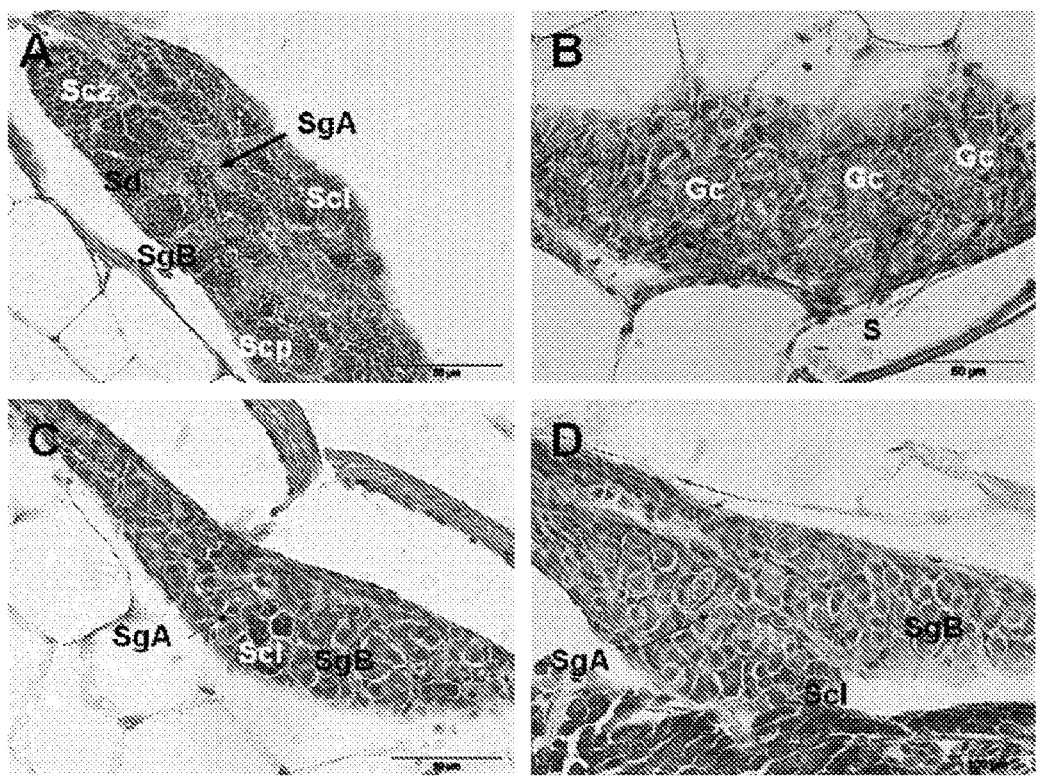

FIG. 6 shows the retardation in zebrafish testis development. FIG. 6A shows the representation of normally developing testis, control male (78 mg, 21.5 mm), 15 days post-treatment. FIG. 6B shows the retarded development in anti-GSDFb-treated male (132 mg, 25.5 mm), 30 days post-treatment: initial phase of differentiation; undifferentiated gonocytes and ingrown stroma are visible. FIG. 6C shows retarded development in anti-GDF9b-treated male (99 mg, 23.8 mm), 30 days post-treatment: early stage of differentiation spermatogonia and start of spermatocyte phase are visible. FIG. 6D shows retarded development in anti-GSDFc-treated male (109 mg, 24.1 mm), 30 days post-treatment: early stage of differentiation spermatogonia and start of spermatocyte phase are visible. SgA—spermatogonia type A, SgB—spermatogonia type B, Scl—spermatocytes, leptotene of meiotic prophase, Scz—spermatocytes, zygotene of meiotic prophase, Scp—spermatocytes at pachytene stage, Sd—spermatids, Gc—undifferentiated gonocytes, S—stroma.

Figure 7:
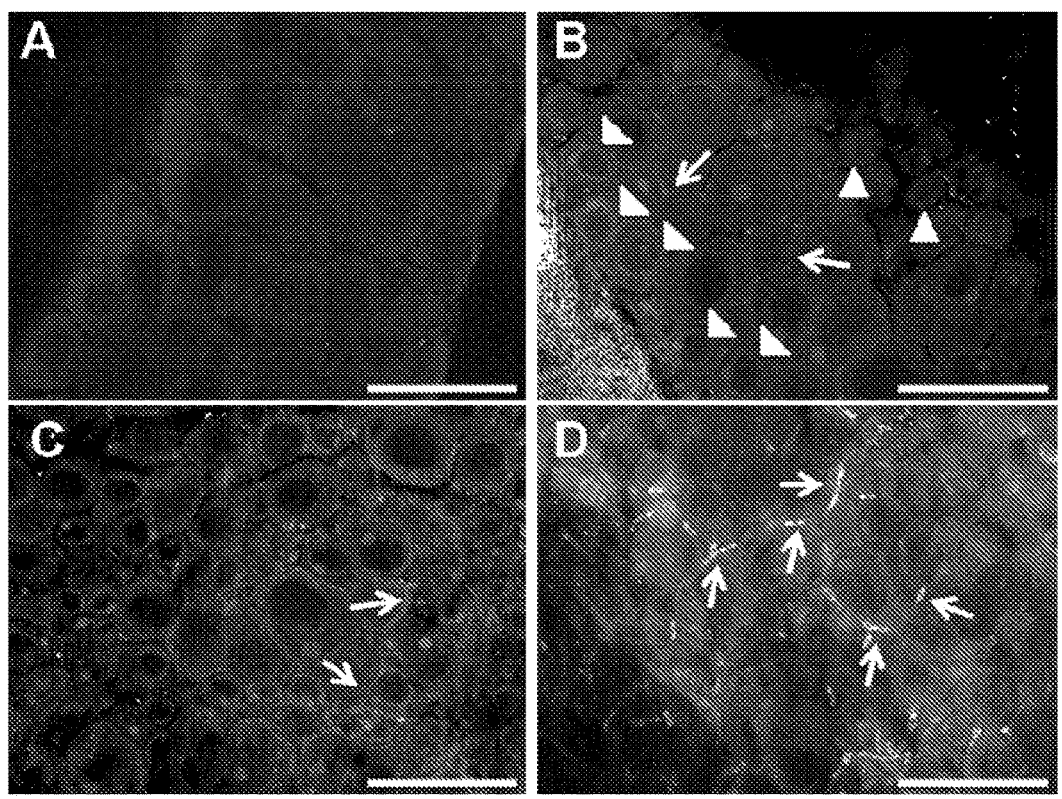

FIG. 7 shows epifluorescent signal indicating the presence of the Bcl2 interacting killer (Bik) apoptotic protein in the ovaries of anti-CD205 zebrafish at 30 dpt. FIG. 7A shows a typical control (fish size 140 mg, 25.7 mm) consisting of stage Ib oocytes with no signal under epifluorescent light. FIGS. 7B to 7D show stage Ib oocytes in two anti-CD205 treated fish (B fish size 71 mg, 21.1 mm; C,D fish size 193 mg, 27.9 mm). White rings surrounding the nuclei indicate the presence of Bik protein in endoplasmic reticulum. Strong apoptotic signal is also detected in follicular cells surrounding oocytes. Arrowheads indicate Bik protein present in the endoplasmic reticulum of the oocyte, resulting in a white ring of expression surrounding the nucleus. Arrows indicate strong Bik expression in follicular cells. Scale bars represent 100 µm.

Protocols are described for zebrafish by way of example but apply, mutatis mutandis, to other fish species and indeed to other animal species.

EXPERIMENTAL SECTION

Example 1—Initial Inhibition of Gonadal Maturation Study

Fish:

Zebrafish are cultured under standard conditions. In order to evaluate the effect of the treatment, germline (ovaries or testes) status is visualized under fluorescent light through expression of fluorescent proteins. A number of zebrafish transgenic lines exist with germline-specific fluorescence protein expression. They include: Tg(vasa:DsRed2-vasa), Tg(kop:EGFP-UTRnanos)erl and Tg(vasa:vasa-EGFP)zf45. Preferred are Tg(vasa:vasa-EGFP)zf45 line for enhanced GFP expression in the germline, and mifta (gene alias: nacre) −/− line for a transparent phenotype. As an alternative to these zebrafish lines, chimeric mRNA construct zebrafish vasa-3'UTR-GFP is used, this is microinjected into zebrafish embryos following the protocol of Saito et al., (2006) International Journal of Developmental Biology 50, 691-700, for visualization of the germline.

IAMs:

The target synthetic antigens, prepared using Invitrogen's Peptide Select Tool to gonadal target proteins as discussed herein, are coupled to a carrier protein as described by Miller at al. (1998) in Vaccine 15, 1858-1862.

Alternatively, polyclonal antibodies against target proteins are prepared for vaccination following the protocols of Pradel et al. (1999) Journal of Neurobiology 39, 197-206.

Immunization:

Antibody-Based technology:

For each target protein, a group of 60 juvenile 6 week old zebrafish are separated into two groups, a control group that are anaesthetized by immersion in 0.08 mg·ml$^{-1}$ buffered MS222 solution and injected intraperitoneally or intramuscularly according to Kinkel et al., 2010, Journal of Vizualized Experiments 42, doi: 10.3791/2126; but modified to use a Hamilton, 10 µl microsyringe attached to a micromanipulator with PBS containing 10 mM sodium phosphate, 120 mM sodium chloride and 2.5 mM potassium chloride. The injection volume is 0.2-5 µl per 0.1 g body mass and injections are performed under a stereomicroscope. The experimental groups are treated as above but injected with PBS containing 3 mg·ml$^{-1}$ polyclonal antisera, or non immune sera or with mAb/pAb to an unrelated protein. These test molecules are commercially available or developed against the desired target using a commercial service.

Antigen-Based Technology:

For an adjuvant trial, 6 week old zebrafish are injected with variety of adjuvants (30 fish per each of the tested adjuvants) to compare survival with respective immune response. The best adjuvant is selected for vaccination trials.

The fish for vaccination are arranged in two groups: one group of 30 fish are sham vaccinated with PBS whereas another group of 30 fish are injected with the target antigen at 6 week post fertilization. The fish are vaccinated, intraperitoneally, as described for the antibody-based technology above. Every three weeks after injection, samples are collected, thus there are three sampling points during the observation period that runs through the maturity cycle of the zebrafish. If more injections (i.e. booster injections) are needed, then they will be repeated weekly in another batch of juveniles. The window for application is roughly from 6 weeks to 8 weeks old. In the most prominent treatment variants, a population of 100 individuals is created for further development to adulthood.

Estimation of Immunization:

Antibody titre is measured using an ELISA method.

Examination of Gonadal Development:

Morphological development of the gonads is evaluated for histology following the method of Maack and Segner (2003) Journal of Fish Biology 62, 895-906. In situ hybridization of DIG-labeled antisense probes to selected gonad-specific genes is performed according to a procedure described by Rodriguez-Mari et al. (2005) Gene Expression Patterns 5, 655-667. Visualization of GFP-labelled germline is performed in vivo under an epifluorescence light microscope, as described by Saito et al. (2006) International Journal of Developmental Biology 50, 691-700. Individuals reaching size and age of sexually mature control fish are tested for reproductive capacity. Evaluation is based on: capacity to produce gametes, quantity (number of laid eggs and volume of collected sperm) and quality (fertilization success of eggs and sperm) of gametes, as compared to control population.

Example 2—Detailed Gonad Maturation Inhibition Study

Materials and Methods

Targets for Immunization:

We have tested six targets as possible candidates for targeted gonad ablation in teleost fishes. Two of those targets, zona pellucida C (ZPC) and riboflavin carrier protein (RCP) have been established as effective in mammalian models. We have used them as a positive control in trial on adult zebrafish.

The four targets have been chosen to test in juvenile zebrafish: insulin-like growth factor 3 (IGF3), growth differentiation factor 9 (GDF9), gonadal soma-derived growth factor (GDSF), and lymphocyte antigen 75 (CD205).

Fish and Husbandry:

All husbandry and experimental procedures were performed in accordance with the Norwegian Regulation on Animal Experimentation (The Norwegian Animal Protection Act, No. 73 of 20 Dec. 1974) and were approved by the National Animal Research Authority (Utvalg for forsøk med dyr, forsøksdyrutvalget, Norway) General License for Fish Maintenance and Breeding (Godkjenning av avdeling for forsoksdyr) no. 17. Fish were housed in a 3-rack stand-alone research recirculating system (Aquatic Habitats, Apopka Fla., USA) and maintained using standard zebrafish procedures (Westerfield (2000) The Zebrafish Book, University of Oregon Press). Water temperature was maintained at 28.0±1.0° C. Adult fish used for research purposes were fed dry flakes (Tetra, Melle, Germany) twice daily. Broodfish were conditioned with SDS 400 zebrafish specific diet (Special Diet Services, Essex, United Kingdom) and freshly hatched *Artemia nauplii* for one month prior to spawning. Juvenile zebrafish were produced using standard breeding techniques (Westerfield, 2000). Post hatch, zebrafish larvae were housed in 1 L tanks with fine mesh baffles and restricted water flow. Starting at 5 days post hatch, fish were weaned using SDS 100 zebrafish specific diet (Special Diet Services). From day 14 to 21 they were given a mix of SDS 100 and *Artemia nauplii*. Post day 21 they were fed only *Artemia nauplii*.

For initial experiments to develop and optimize procedures for antigen delivery, adult zebrafish of mixed strain were obtained from Febo Norge AS (Oslo, Norway). They were reproduced and both adults and juveniles were used for experiments.

For the main experiment, that is vaccination of juvenile zebrafish, adult zebrafish from three inbred strains (TAB, Nacre −/−, tg(vas::egfp)) were obtained from the Norwegian School of Veterinary Science (Oslo, Norway). The TAB line (Tuebingen/AB) was reference wild-type strain. The tg(vas::egfp) line were offspring from a previously established transgenic line (Krovel and Olsen (2002) Mechanisms of Development, 116, 141-50). Broodfish were housed in 10 L tanks at a density of 20 fish/tank with a 1:1 sex ratio.

Injection Survivability Trial:

In order to examine the practicality of intraperitoneal injection as a vaccine delivery method, both juvenile and adult fish were injected and monitored for survival for 7 days post injection (dpi). For the juvenile trial, 22 fish at 8 weeks post fertilization (27.4 mm±15.2, average±standard deviation) were randomly divided into two groups. The treatment group received an injection of phosphate buffered saline solution (PBS; Sigma-Aldrich, Oslo, Norway), while the control group underwent a mock injection. A cold-water bath was used as anaesthetic as previously described by Kinkel et al. (2010) J. Vis. Exp., e2126. Experimental fish were left in the water until they were unresponsive to physical stimuli. Fish were removed from the bath and weighed on a moist paper towel before being transferred to a wet sponge inside a Petri dish. Each fish had PBS injected into the perioneal cavity using a 10 µL syringe (Cat. no. 7635-01, Hamilton, Bonaduz, Switzerland) equipped with a 34 g needle (Cat. no. 207434, Hamilton). The initial fish was injected with 4.0 µL PBS but immediately showed signs of exopthalmia. While this fish recovered and survived past day 0, subsequent injection volumes were lowered to 1.0 µL. After injection, fish were returned to a recovery tank with a water temperature of 25° C. Control fish underwent a mock injection procedure which included anaesthesia by cold water, being weighed, placed on the wet sponge for 10 seconds, and then moved to the recovery tank.

In the adult fish trial, two-year-old zebrafish were divided into five groups: mock injection (NC), PBS, Freund's incomplete adjuvant (FIA; Cat. no. F5506, Sigma-Aldrich) emulsified 1:1 with PBS, Freund's complete adjuvant (FCA; Cat. no. F5881, Sigma-Aldrich) emulsified 1:1 with PBS, and FCA emulsified 1:1 with maleimide activated keyhole limpet hemocyanin (KLH; Cat. no. K0383, Sigma-Aldrich) in PBS (1.0 mg/mL). The injection procedure was as previously described except that the injection volume was increased to 5.04 and was administered with a 50 µL syringe (Cat. no. 7637-01, Hamilton, Bonaduz, Switzerland) equipped with a 26 g needle (Cat. no. 7804-04, Hamilton). Survival over 7 days was recorded.

Adult Fish Vaccination Trial:

Vaccine Preparation:

The experimental vaccines consisted of a synthetic peptide conjugated to KLH. Table 1 below presents the amino acid sequences of the peptides used for the vaccination trial in adult zebrafish. Each peptide was chosen from the complete respective amino acid sequence based on predicted antigenicity (Hopp and Woods (1981) Proc. Nac. Acad. Sci 78, 3824-3828). The peptides were commercially synthesized at >80% purity (Thermo Scientific, Ulm, Germany) and conjugated to KLH using a maleimide activated conjugation kit following the manufacturer's protocol (Cat. no. MBK1, Sigma Aldrich). After conjugation, the protein conjugates were isolated through column chromatography (Sephadex G-25M, Cat. no. B4783, Sigma Aldrich) and eluted in PBS. Coupling efficiency was determined by comparing the absorbance at 412 nm from a cysteine standard assay with each peptides cysteine absorbance values before and after conjugation. Final protein concentration was estimated by measuring absorbance at 280 nm. Peptide-KLH conjugates were stored at −20° C. until immediately before use. After thawing, the conjugates were diluted in PBS (1.0 mg/mL) and emulsified by vortex at a 1:1 ratio with FCA.

TABLE 1

| Target Protein | Abbreviation | Accession | Peptide sequence |
|---|---|---|---|
| Lymphocyte antigen 75 | CD205 | XP_695257 | FKTDG FEDDG DDSEE C (SEQ ID NO: 1) |
| Insulin-like growth factor 3 | IGF3 | NP_001108522 | LYCAK SKKVR RDVPA C (SEQ ID NO: 2) |
| Riboflavin carrier protein | RCP | NP_001018566 | RVQEG DPEEL DTTKS C (SEQ ID NO: 3) |

TABLE 1-continued

| Target Protein | Abbreviation | Accession | Peptide sequence |
|---|---|---|---|
| Zona pellucida glycoprotein C | ZPC | CAH69084 | ASKFL PRVKD DKLRF C (SEQ ID NO: 4) |

Immunization:

In total, 485 zebrafish (42.8±2.5 mm, average±standard deviation) were immunized with one of the four treatments or a PBS/FCA control. Because of a limited availability of male fish, only female zebrafish were considered for this experiment. Each treatment group initially consisted of 105 fish whereas the control group had 65 fish. Prior to immunization, zebrafish were anaesthetized in a bath of 150 mg/L MS-222 (Tricaine; Sigma, Oslo, Norway) buffered with 150 mg/L sodium bicarbonate (NaHCO$_3$). Fish were considered in surgical anaesthesia (stage III) when they became unresponsive to physical stimuli but maintained opercular movement (Matthews & Trevarrow (2002) Lab. Anim., 31, 34-40). Fish were removed from the bath and placed on a wet sponge inside a petri dish. Injections of the vaccine were made intraperitoneally immediately below the pectoral fin. All injections were 10.0 μL (5.0 μg peptide-KLH) volume.

Sampling:

Zebrafish were sampled immediately prior to immunization. Treatment fish were then sampled every 10 days for 30 days, whereas control fish were sampled on day 20. Prior to sampling, fish received an overdose of buffered MS-222 (200 mg/L) and remained in the solution for 10 minutes following cessation of opercular movement. Upon removal from the bath, the fish were patted dry and weight and fork length measurements were taken. To ensure mortality the fish were then decapitated before opening the body cavity. The bodies were briefly washed with PBS before being fixated in 4% paraformaldehyde (pH 7.4) solution overnight at 4° C. The following day, the tissues were washed in PBS and the gonads were excised and weighed.

Juvenile Zebrafish Vaccination Trial:

Vaccine Preparation:

Peptides for four target protein were designed based on predicted antigenicity, as detailed in Hopp and Woods (1981) PNAS, 78, 3824-8. Table 2 below presents the amino acid sequences of the peptides used for the vaccination trial in juvenile zebrafish. Custom peptides were synthesized and conjugated to KLH by Thermo Fisher Scientific. Upon arrival, lyophilized peptides were dissolved in PBS to make a stock solution of either 10.0 or 5.0 mg/L, depending on protein solubility. Treatments consisted of either a single antigen or a combination of antigens emulsified 1:1 in FCA.

TABLE 2

| Target Protein | Abbreviation | Accession | Peptide sequence(s) |
|---|---|---|---|
| Insulin-like growth factor 3 | IGF3 | NP_001108522 | A) LYCAK SKKVR RDVPA C (SEQ ID NO: 5) B) EGARA RCGRE LVDDC (SEQ ID NO: 6) C) RSGGP RSRGK GIVDQ C (SEQ ID NO: 7) |
| Gonadal soma-derived factor | GSDF | ABZ01522 | B) KSLHL PKEPS NSLSQ C (SEQ ID NO: 8) C) SLKNS IHSPP GNSSL C (SEQ ID NO: 9) |
| Growth/differentiation factor 9 | GDF9 | NP_001012383 | B) YSFDH NHLSP FSLL C (SEQ ID NO: 10) C) QAHKK DIHLL INLT C (SEQ ID NO: 11) |
| Lymphocyte antigen 75 | CD205 | XP_695257 | B) NENDT ESTVR DVYKP C (SEQ ID NO: 12) C) RRNPN TNNNW EWSDG C (SEQ ID NO: 13) |

Immunization:

Juvenile zebrafish from each inbred strain were selected between five to seven weeks post hatch based on a total length of approximately 15 mm. In total, 384 fish (15.5±2.8 mm) were immunized with one of six treatments or a PBS/FCA control (Table 3). The anti-IGF3 treatment consisted of all three peptides combined (i.e. IGF3(A), IGF3(B) and IGF(C) as shown in Table 2) and resulted in each individual peptide having a final vaccine concentration of 0.83 mg/mL. For anti-GSDF and anti-GDF9 treatments, the (B) and (C) peptides were injected individually and had a final concentration of 2.5 mg/mL. Peptides (A) in both anti-GSDF and anti-GDF9 treatments were not used. Because of high solubility, CD205(B) and CD205(C) peptides were combined and retained a final concentration of 2.5 mg/mL in anti-CD205 treatment. Selected fish were anesthetized in a Petri dish of tank water containing 50 mg/L MS-222 (Tricaine; Sigma, Oslo, Norway) buffered with equal parts sodium bicarbonate. Each anesthetized fish was first individually photographed and measured for total length using a Zeiss Axio Zoom v.16 stereomicroscope. Fish from the tg(vas::egfp) strain were also screened for a green fluorescent protein signal before being transferred to a wet sponge and injected with 2.0 μL of the experimental vaccine using a 50 μL syringe equipped with a 34 g needle. Post injection, fish were transferred to a Petri dish of tank water to monitor recovery for 10 min before returning to a housing tank.

At 15 days post injection, each fish from all treatments except for anti-IGF3 received a booster vaccination. Some control fish paired with anti-IGF3 also did not receive a booster. The same protocol was followed for the booster injection as before except the vaccination volume was reduced to 1.0 μL and FIA was used as the adjuvant.

Table 3 below provides the distribution of fish used for juvenile vaccination trial. Fish from three inbred strains were used for the experiment: TAB (T), nacre −/−(N), and tg(vas::egfp) (V). Treatment name consists of the target protein in uppercase and the specific antigen(s) described in Table 2 in parenthesises.

TABLE 3

| Treatment | #Fish | Initial length (mm ± SD) | 15 D Booster (Y/N) | # Fish Sampled 15 D | #Fish Sampled 30 D |
|---|---|---|---|---|---|
| Control | 38 T | 15.7 ± 3.1 | Y 80/105 | 13 T | 22 T |
|  | 19 N |  | N 25/105 | 14 N | 0 N |
|  | 48 V |  |  | 20 V | 25 V |
| IGF3 (A + B + C) | 11 T | 14.9 ± 2.9 | N | — | 8 T |
|  | 3 N |  |  | — | 3 N |
|  | 12 V |  |  | — | 11 V |

TABLE 3-continued

| Treatment | #Fish | Initial length (mm ± SD) | 15 D Booster (Y/N) | # Fish Sampled 15 D | #Fish Sampled 30 D |
|---|---|---|---|---|---|
| GDF9 (B) | 19 T | 15.6 ± 2.0 | Y | 6 T | 7 T |
|  | 25 N |  |  | 10 N | 7 N |
|  | 23 V |  |  | 10 V | 11 V |
| GDF9 (C) | 19 T | 15.6 ± 2.0 | Y | 9 T | 10 T |
|  | 5 N |  |  | — | 3 N |
|  | 18 V |  |  | — | 15 V |
| GSDF (B) | 13 T | 16.0 ± 3.2 | Y | 6 T | 6 T |
|  | 7 N |  |  | 4 N | 3 N |
|  | 20 V |  |  | 8 V | 12 V |
| GSDF (C) | 15 T | 15.3 ± 1.9 | Y | 6 T | 8 T |
|  | 3 N |  |  | 1 N | 2 N |
|  | 19 V |  |  | 9 V | 9 V |
| CD205 (B + C) | 23 T | 16.5 ± 2.9 | Y | 9 T | 12 T |
|  | 40 V |  |  | 15 V | 21 V |

Fish Sampling:

At 15 and 30 days post injection the zebrafish were sampled for quantitative real-time PCR (qPCR), histology and immunohistochemistry (IHC). Prior to sampling all fish were euthanized in buffered MS-222 (100 mg/L) so they could be photographed, screened for GFP signal, weighed and measured (total length).

Because of their genetic homogeneity and established reputation as a wild-type reference strain, TAB strain fish were used solely for qPCR analysis. For each fish destined for qPCR, gonadal mRNA signal was improved by removing as much unrelated tissue as possible. Because of the delicate nature of the juvenile gonad, it could not be dissected on its own. Instead, the digestive system, heart, and head kidney were removed along with the head and tail. This left only the trunk muscle tissue, swim bladder, kidney, and gonadal tissues in the samples. Each of these samples was placed in a 1.5 mL eppendorf tube and frozen in liquid nitrogen. Samples were stored at −80° C. until RNA extraction.

Fish from the nacre −/− and tg(vas::egfp) strains were used for visual observations. When sampling, after initial measurements were taken, fish destined for histology and IHC were decapitated immediately posterior to the pectoral fins and truncated. The body cavity was cut open before placing the fish in either Bouin's or 4% PFA solution. Samples for both techniques were left to fixate overnight at 4° C. Fixed samples were dehydrated in a gradient series of ethanol (from 50% up to 100%).

Quantitative Real Time PCR:

Total RNA was extracted using TRIzol Reagent (Invitrogen, Paisley, U.K.) following the manufacturer's protocol. RNA integrity was first assessed using electrophoresis on a 1% (w/v) agarose gel. Suitable samples were then quantified using NanoDrop ND-1000 (Thermo scientific, Saven & Werner AS, Kristiansand, Norway). Approximately 1 μg of total RNA was used for cDNA synthesis using the Quanti-Tect reverse transcription kit (Qiagen, Nydalen, Sweden). All samples were treated with the gDNA wipeout buffer supplied with the QuantiTect reverse transcription kit for 5 minutes to remove genomic DNA contamination. 20-fold dilutions of cDNA were used for further analysis.

The six genes selected for qPCR analysis were: T-Cell receptor alpha constant (tcrac), immunoglobulin kappa constant (igkc), vasa (vasa), gonadal somatic cell derived factor (gsdt), inhibin alpha (inhα), and anti-Müllerian hormone (amh). The genes used for reference were beta actin (β-actin) and elongation factor 1 alpha (ef1α). Tcrac and igkc were both established as markers for T and B-cells, respectively (Lam et al. (2004) Comp. Immunol., 28, 9-28). Vasa is a conserved germ cell marker (Yoon et al. (1997) Development, 124, 3157-65), whereas gsdf, inhα, and amh are specifically expressed in granulosa and Sertoli cells (Gautier et al. (2011) Gene, 472, 7-17, Poon et al. (2009) Reproduction, 138, 709-19, Shibata et al. (2010), Gene Expression Patterns, 10, 283-9 and Rodriguez-Mari et al. (2005) PLoS Genet., 6, e1001034). Specific primers for each target gene for qPCR amplification were either designed manually using Netprimer software (http://www.premierbiosoft.com/netprimer) or taken from literature. In particular, the β-actin and ef1α primers have previously been used as detailed in Tang et al. (2007) Acta Biochimica et Biophysica Sinica, 39, 384-90, and the inhα primer has previously been used in Poon et al. (2009). Table 4 presents the nucleotide sequences of the primers used. When possible, primers were designed to span one intron/exon border to avoid amplification of potential contaminating genomic DNA (Fernandes et al. (2008) Biochem. Mol. Biol., 150, 23-32).

TABLE 4

| Gene | GenBank | 5'→3' upstream primer | 5'→3' downstream primer | E% | $R^2$ | Size |
|---|---|---|---|---|---|---|
| β-actin | ENSDART00000055194 | CGAGCTGTCTTCCCATCCA (SEQ ID NO: 14) | TCACCAACGTAGCTGTCTTTCTG (SEQ ID NO: 15) | 94.1 | 0.999 | 84 |
| ef1α | ENSDART00000023156 | CTGGAGGCCAGCTCAAACAT (SEQ ID NO: 16) | ATCAAGAAGAGTAGTACCGCTAGCATTAC (SEQ ID NO: 17) | 93.9 | 0.999 | 85 |
| tcrac | AF246178 | CACAACGAGTTCAACATTACCGA (SEQ ID NO: 18) | CCAGAAGATGCCCAGTGACAA (SEQ ID NO: 19) | 89.8 | 0.999 | 194 |
| igkc | ENSDARG00000078975 | TGGATGTTGGCAGCGTCAC (SEQ ID NO: 20) | GCACTGCTCTCCTGAAACCTG (SEQ ID NO: 21) | 76.6 | 0.999 | 172 |
| vasa | NM_131057 | TCAGAGCAACAGGTAATGAGC (SEQ ID NO: 22) | CTACAGATGTGGCGACCAGAAC (SEQ ID NO: 23) | 90.5 | 0.998 | 195 |

TABLE 4-continued

| Gene | GenBank | 5'→3' upstream primer | 5'→3' downstream primer | E% | $R^2$ | Size |
|---|---|---|---|---|---|---|
| gsdf | NM_001114668 | GAACGCTCCTGAAT CCACAGAC (SEQ ID NO: 24) | AATGACTCCCGCAGAT GCTC (SEQ ID NO: 25) | 90.5 | 0.999 | 210 |
| inhα | NM_001045204 | AGCCTCCTCTGCCA GTGTTG (SEQ ID NO: 26) | AGCATCAGAAGAGTGG TCAGGTA (SEQ ID NO: 27) | 97.7 | 0.996 | 188 |
| amh | AY721604 | TGCTCCTGTTCAGT GTCAATCC (SEQ ID NO: 28) | ATGTCTCAACCATCGT CTTCAGT (SEQ ID NO: 29) | 77.5 | 0.992 | 180 |

The RT-qPCR was performed on LightCycler 480 (Roche, Mannheim, Germany) using 96-well plates (Roche). SYBR green-based detections were done under the thermal cycle conditions of 95° C. for 15 min, followed by 45 cycles of 95° C. for 15 s, 63° C. for 20 s and 72° C. for 20 s. All samples were run in duplicate, together with minus reverse transcriptase, no template and a positive plate control. 5-point standard curves (dilutions 1:1-1:81) were used to calculate the efficiency of the PCR reaction. The reaction specificity was evaluated by melting curve analysis. Cycle threshold ($C_T$) values were determined using the LightCycler® 480 software with a level of fluorescence intensity set to one. The reference genes (β-actin and ef1α) were examined for data normalization using geNorm (Vandesompele et al. (2002) Genome Biology, 3, 34.1-34.11). Stability values were calculated to be 0.796. Raw qPCR data for the target genes were then corrected by the geometric average of the reference genes.

Gonad Histology:

Previously fixed samples were examined through traditional histology, or as a whole gonad using optical sectioning. For the histology, samples were embedded in paraffin wax and systematically sectioned (5-7 μm thick sections) using a rotary microtom (Microm HM355S, MICROM International GmbH, Germany). Sectioning was followed by microscopic observation to optimize the appearance of the gonads in the sections. To improve the adhesion of the specimens onto slides, the slides were coated with (3-aminopropyl) triethoxysilane (Sigma-Aldrich). Samples were stained with Heamatoxylin-Eosin in the Robot Slide Stainer (Microm HMS 760X, Thermo Scientific, Germany) and mounted using Pertex mounting media (Leica Biosystems). Evaluation and imaging on the samples done by use of the light microscope Olympus BX 51 (OLYMPUS Optical Co. GmbH, Germany) and Olympus Imaging software Cell B (Olympus SoftImage Solution, GmbH, Germany).

Some individuals from the tg(vas:egfp) strain were not sectioned. Instead, the fixed gonads were rehydrated in PBS, dissected from the whole fish, and placed on a glass slide with a drop of 50% glycerol/PBS. A cover slip was placed over the gonad and optical sectioning was performed using a AxioZoom.V16 microscope equipped with the ApoTome.2 (Zeiss, Germany).

Immunohistochemistry (IHC):

Control and anti-CD205 ovaries from the 30 dpt group were also examined using whole mount IHC. Whole ovaries that were previously imaged using optical sectioning were stained for the presence of Bcl2-interacting-killer (Bik) protein. Bik is a pro-apoptotic protein localized to the endoplasmic reticulum which is normally suppressed by survival-promoting factors.

The whole mount IHC procedure was performed basically as described by Draper (2012) Meth. Mol. Biol., 85(3), 615-25 with the following modifications: the primary antibody used was rabbit polyclonal IgG specific for anti-zebrafish Bik protein (Anaspec, Belgium). The primary antibody was diluted 1:150 and administered overnight at 4° C. The secondary antibody used was Alexa Fluor® 594 goat anti-rabbit IgG at a 1:500 dilution for 5 hours at room temperature. After the completion of the IHC procedure the gonads were imaged using an AxioZoom.V16 microscope equipped with the ApoTome.2 and DsRed filter.

Statistical Analyses:

The data are presented as averages±standard deviations. The procedures were according to Zar (1999) Biostatistical Analysis, New Jersey, Prentice Hall. To test the effects of treatments on fish weight, length and relative values of gene expression, ANOVA was used. Homogeneity of variances was tested using Levene's test. Fisher's least significant difference test was used as a post-hoc test to investigate differences between groups. Pearson's product-moment correlation coefficient r was used to investigate relationships between gene expressions. Significant effects were considered at $p<0.05$.

Results

Injection Survivability Trial:

Table 5 below provides the survival of zebrafish over 7 days post intraperitoneal injection with PBS (adjuvant control), Freund's incomplete adjuvant (FIA) emulsified 1:1 with PBS, Freund's complete adjuvant (FCA) emulsified 1:1 with PBS, and FCA emulsified 1:1 with keyhole limpet hemocyanin (KLH) in PBS. Mock groups (NC) were also created.

TABLE 5

| Treatment | Survival Day 0 | Day 1 | Day 3 | Day 7 | % Survival |
|---|---|---|---|---|---|
| Juvenile | | | | | |
| PBS | 10/11 | 10/11 | 9/11 | 9/11 | 81.8 |
| NC | 11/11 | 11/11 | 11/11 | 11/11 | 100 |
| Adult | | | | | |
| PBS | 8/8 | 7/8 | 7/8 | 6/8 | 75 |
| FIA | 6/6 | 5/6 | 5/6 | 4/6 | 66.7 |
| FCA | 7/7 | 7/7 | 7/7 | 7/7 | 100 |
| FCA/KLH | 15/16 | 15/16 | 15/16 | 15/16 | 93.8 |
| NC | 21/21 | 20/21 | 19/21 | 16/21 | 76.2 |

Immediately post injection most treatments showed 100% survival, with only 1 individual dying each in the juvenile PBS and adult FCA/KLH groups. Mortalities were observed in the following days with the most significant observed in the adult FIA, PBS, and NC treatments.

Adult Zebrafish Vaccination Trial:

Table 6 below shows total weight, fork length, and gonadosomatic index (GSI%) of adult zebrafish females vaccinated with Zona pellucida C (ZPC), Lymphocyte antigen 75 (CD205), Insulin-like growth factor 3 (IGF3), and Riboflavin carrier protein (RCP). Sampling was performed at day 0 (Control), 10, 20 and 30 days post-treatment. At 20 days post-treatment, a PBS-injected control was additionally performed. N=number of fish per treatment; S.D.=standard deviation. Underline font indicates values significantly lower than Controls, whereas bold font indicates values significantly higher than Controls (p<0.05).

Effect of Treatment on Fish Growth:

Fish at day 0, just before the injection, were measured for length only, to minimize their exposure to out-of-water procedures. At days 15 and 30, both length and weight were measured. Fish at the day 0 were homogenous and ANOVA found no significant differences in length. At day 15, fish from anti-GSDFc treatment were significantly lighter than controls, but no significant differences in length were recorded. At day 30, more distinct retardation in growth rate was observed: fish from 4 out of 6 treatment variants were significantly lighter than in controls; of them, fish from two variants (anti-GSDFc and anti-CD205bc) were significantly shorter than control fishes (FIG. 1).

TABLE 6

| | Weight (g) | | | Fork length (mm) | | | GSI (%) | | |
|---|---|---|---|---|---|---|---|---|---|
| | N | Average | S.D. | N | Average | S.D. | N | Average | S.D. |
| ZPC 10 days | 29 | 0.90 | 0.13 | 29 | 42.0 | 1.5 | 29 | 8.2 | 3.3 |
| ZPC 20 days | 28 | 0.95 | 0.13 | 28 | 43.0 | 2.1 | 28 | 9.3 | 2.6 |
| ZPC 30 days | 20 | 1.11 | 0.17 | 20 | 43.6 | 2.0 | 20 | 13.4 | 3.7 |
| CD205 10 days | 27 | 0.89 | 0.12 | 27 | 41.9 | 1.6 | 26 | 9.0 | 3.7 |
| CD205 20 days | 28 | 0.96 | 0.17 | 28 | 43.3 | 2.4 | 27 | 10.6 | 2.6 |
| CD205 30 days | 27 | 1.02 | 0.19 | 27 | 43.1 | 1.8 | 27 | 10.1 | 2.4 |
| IGF3 10 days | 20 | 1.01 | 0.14 | 20 | 43.8 | 2.2 | 20 | 12.5 | 4.7 |
| IGF3 20 days | 25 | 0.97 | 0.12 | 25 | 43.1 | 2.3 | 25 | 12.9 | 4.2 |
| IGF3 30 days | 28 | 1.13 | 0.17 | 28 | 44.1 | 2.0 | 22 | 14.4 | 4.7 |
| RCP 10 days | 17 | 0.95 | 0.16 | 17 | 42.6 | 2.2 | 17 | 12.2 | 3.5 |
| RCP 20 days | 16 | 1.00 | 0.19 | 16 | 42.5 | 2.1 | 16 | 12.8 | 3.6 |
| RCP 30 days | 17 | 1.04 | 0.15 | 17 | 43.3 | 1.7 | 17 | 14.6 | 3.6 |
| Control | 32 | 0.98 | 0.12 | 32 | 42.8 | 2.5 | 26 | 12.3 | 3.5 |
| PBS control 20 days | 18 | 1.01 | 0.21 | 18 | 43.2 | 2.7 | 18 | 13.8 | 4.7 |

At day 10 post-treatment, significant effect of treatment on fish weight ($F_{(4,120)}=4.0$, p=0.004) and GSI % ($R_{(4,113)}=7.8$, p<0.001) was found. Fish from anti-ZPC and anti-CD205 treatments had significantly lower weight, comparing to controls; length of treated fish was not different from controls. Loss of total weight in anti-ZPC and anti-CD205 treatments was resulting from loss in gonadal weight, because the GSI % of fish in both treatments was significantly lower than in controls.

At day 20 post-treatment, no significant differences in weight and length of fish were found. The effect of treatment on GSI % was significant ($F_{(5,134)}=5.2$, p<0.001). Fish from anti-ZPC variant had significantly lower GSI % than controls. GSI % of fishes from anti-ZPC and anti-CD205 treatments was significantly lower than GSI % of PBS-injected controls. Other treatments did not differ from either non-injected or PBS-injected controls.

At day 30 post-treatment, significant effect of treatment on fish weight ($F_{(4,119)}=4.2$, p=0.003) and GSI ($F_{(4,107)}=8.8$, p<0.001) was observed. Fish from ZPC and IGF3 treatments were significantly heavier than control fishes; however, their GSI did not differ significantly from controls. GSI of fish treated with CD205 was significantly lower than in any other treatment, also significantly lower than in controls.

Juvenile Zebrafish Vaccination Trial:

Sex Distribution:

Comparisons for sex, weight and length were made using the reference TAB strain only. No effect of treatments was found on sex distribution. In general, the proportion females: males was 55:45, not deviating from the expected 50:50 ratio.

Sex-Biased Gene Expression:

Table 7a and 7b below shows sex-biased expression of transcripts in the juvenile zebrafish gonads (n=113). Relative gene expression in male and female gonads is given along with fold change. Significant bias female/male is marked using underline font and significant male/female bias is marked using bold font.

Intermediate or transition phase gonads were excluded from this analysis.

TABLE 7a

| | tcrac | | igkc | | vasa | |
|---|---|---|---|---|---|---|
| | mean | SD | mean | SD | mean | SD |
| Male | 1239 | 1144 | 2249 | 2235 | 2075 | 1118 |
| Female | 4062 | 2197 | 1609 | 1025 | 4596 | 1360 |
| Fold change | 3.3 | | 1.4 | | 2.2 | |

TABLE 7b

| | gsdf | | inhα | | amh | |
|---|---|---|---|---|---|---|
| | mean | SD | mean | SD | mean | SD |
| Male | 5612 | 2984 | 7210 | 4026 | 10110 | 7572 |
| Female | 770 | 147 | 3753 | 2279 | 475 | 92 |
| Fold change | 7.3 | | 1.9 | | 21.3 | |

Five out of six investigated genes showed significantly sex-biased expression in juvenile zebrafish gonads: tcrac ($F_{(2,112)}$=6.7, $p<0.001$), vasa ($F_{(2,113)}$=21.6, $p<0.001$), gsdf ($F_{(2,113)}$=54.3, $p<0.001$), inhα ($F_{(2,110)}$=10.8, $p<0.001$), and amh ($F_{(2,112)}$=33.0, $p<0.001$). Expression of tcrac and vasa was female-biased, whereas expression of gsdf, inhα and amh was male-biased. No significant effect of sex was found only in igkc expression.

Table 8a to Table 8c below show correlations (Pearson's product-moment correlation coefficient r) between the relative expressions of the investigated genes (all variants, n=111). Significant r values ($p<0.05$) are marked with bold font. Correlations within female-transcripts are marked in double-underlined font and correlations within male-biased transcripts are marked with underlined font.

TABLE 8a

| All variants | | | | | |
|---|---|---|---|---|---|
| | igkc | vasa | gsdf | inhα | amh |
| tcrac | −0.24 | 0.78 | −0.52 | −0.14 | −0.43 |
| igkc | | −0.25 | 0.32 | 0.12 | 0.15 |
| vasa | | | −0.55 | 0.03 | −0.37 |
| gsdf | | | | 0.65 | 0.84 |
| inhα | | | | | 0.84 |

TABLE 8b

| Controls | | | | | |
|---|---|---|---|---|---|
| | igkc | vasa | gsdf | inhα | amh |
| tcrac | −0.10 | 0.79 | −0.53 | −0.25 | −0.46 |
| igkc | | −0.15 | 0.31 | 0.15 | 0.19 |
| vasa | | | −0.54 | −0.07 | −0.37 |
| gsdf | | | | 0.73 | 0.85 |
| inhα | | | | | 0.91 |

TABLE 8c

| Treatments only | | | | | |
|---|---|---|---|---|---|
| | igkc | vasa | gsdf | inhα | amh |
| tcrac | −0.29 | 0.78 | −0.53 | −0.09 | −0.44 |
| igkc | | −0.28 | 0.36 | 0.16 | 0.21 |
| vasa | | | −0.57 | 0.08 | −0.41 |
| gsdf | | | | 0.61 | 0.85 |
| inhα | | | | | 0.76 |

The pattern of correlations was similar in controls (n=31) and in the treated groups (n=80). Correlations between transcript relative abundances followed this pattern: testis-abundant gsdf, inhα and amh showed high positive correlation with each other in both control and treated groups, whereas ovary-abundant tcrac and vasa correlated highly and positively. Therefore, analysis of the effect of vaccination on gene expression has been conducted on males and females separately.

Effect of Vaccination on Gene Expression in Juvenile Zebrafish Gonad:

Tables 9a and 9b show gene expression in juvenile zebrafish gonads after vaccination with the antigens. Table 9a shows the gene expression 15 days post-treatment, and Table 9b shows the gene expression 30 days post-treatment. A booster injection was applied to all except anti-IGF3 treatments after 15 days. Normalized relative average values and standard deviations are given. Upregulation and downregulation in transcript abundance, expressed as a fold-change of the control values (F-c), are marked as a positive number or a negative number, respectively. Significant differences between treatment and control values are marked with bold font. Gene expression in the anti-IGF3 treatment was compared to controls which did not receive the booster injection (no booster).

TABLE 9a

| | tcrac | | | igkc | | | vasa | | |
|---|---|---|---|---|---|---|---|---|---|
| males | mean | SD | F-c | mean | SD | F-c | mean | SD | F-c |
| Control | 1050 | 1131 | | 1535 | 2052 | | 1312 | 1604 | |
| GSDFb | 678 | 214 | −1.5 | 2881 | 1022 | 1.9 | 951 | 867 | −1.4 |
| GSDFc | 496 | 426 | −2.1 | 2732 | 2998 | 1.8 | 781 | 506 | −1.7 |
| GDF9c | 806 | 489 | −1.3 | 2007 | 2033 | 1.3 | 657 | 455 | −2.0 |
| GDF9b | 416 | 110 | −2.5 | 430 | 459 | −3.6 | 1143 | 1281 | −1.1 |
| CD205bc | 654 | 239 | −1.6 | 4227 | 3754 | 2.8 | 347 | 421 | −3.8 |

| | gsdf | | | inhα | | | amh | | |
|---|---|---|---|---|---|---|---|---|---|
| males | mean | SD | F-c | mean | SD | F-c | mean | SD | F-c |
| Control | 4922 | 3236 | | 3103 | 3089 | | 5081 | 3455 | |
| GSDFb | 5966 | 1755 | 1.2 | 5091 | 3922 | 1.6 | 9187 | 5564 | 1.8 |
| GSDFc | 5631 | 2271 | 1.1 | 5511 | 4831 | 1.8 | 7078 | 3649 | 1.4 |
| GDF9c | 4868 | 979 | −1.0 | 1776 | 258 | −1.7 | 6944 | 3604 | 1.4 |
| GDF9b | 4767 | 605 | −1.0 | 4376 | 3711 | 1.4 | 8032 | 5457 | 1.6 |
| CD205bc | 4031 | 916 | −1.2 | 2115 | 1756 | −1.5 | 4498 | 2493 | −1.1 |

| | tcrac | | | igkc | | | vasa | | |
|---|---|---|---|---|---|---|---|---|---|
| females | mean | SD | F-c | mean | SD | F-c | mean | SD | F-c |
| Control | 3498 | 2824 | | 938 | 678 | | 3546 | 2406 | |
| GSDFb | 4014 | 354 | 1.1 | 1184 | 1003 | 1.3 | 4063 | 717 | 1.1 |
| GSDFc | 2681 | 296 | −1.3 | 1777 | 2020 | 1.9 | 3008 | 361 | −1.2 |
| GDF9c | 880 | 685 | −4.0 | 789 | 503 | −1.2 | 1096 | 758 | −3.2 |
| GDF9b | 2861 | 1063 | −1.2 | 371 | 382 | −2.5 | 2156 | 1024 | −1.6 |

TABLE 9a-continued

| | | | | | | | | | |
|---|---|---|---|---|---|---|---|---|---|
| CD205bc | 1868 | 1173 | −1.9 | 4125 | 2565 | 4.4 | 2267 | 558 | −1.6 |

| | gsdf | | | inhα | | | amh | | |
|---|---|---|---|---|---|---|---|---|---|
| females | mean | SD | F-c | mean | SD | F-c | mean | SD | F-c |
| Control | 1495 | 825 | | 1717 | 1110 | | 303 | 154 | |
| GSDFb | 900 | 232 | −1.7 | 2216 | 571 | 1.3 | 446 | 36 | 1.5 |
| GSDFc | 1550 | 185 | 1.0 | 2348 | 510 | 1.4 | 393 | 156 | 1.3 |
| GDF9c | 1525 | 886 | 1.0 | 812 | 625 | −2.1 | 183 | 111 | −1.7 |
| GDF9b | 982 | 272 | −1.5 | 1461 | 965 | −1.2 | 290 | 142 | −1.0 |
| CD205bc | 1562 | 707 | 1.0 | 1656 | 429 | −1.0 | 346 | 184 | 1.1 |

TABLE 9b

| | tcrac | | | igkc | | | vasa | | |
|---|---|---|---|---|---|---|---|---|---|
| males | mean | SD | F-c | mean | SD | F-c | mean | SD | F-c |
| Control | 545 | 328 | | 2037 | 2078 | | 1519 | 469 | |
| GSDFb | 893 | 399 | 1.6 | 3658 | 75 | 1.8 | 949 | 341 | −1.6 |
| GSDFc | 1468 | 1495 | 2.7 | 2534 | 1547 | 1.2 | 1662 | 1561 | 1.1 |
| GDF9c | 819 | 433 | 1.5 | 5040 | 1334 | 2.5 | 889 | 441 | −1.7 |
| GDF9b | 941 | 472 | 1.7 | 4999 | 774 | 2.5 | 1184 | 769 | −1.3 |
| CD205bc | 816 | 411 | 1.5 | 3844 | 2450 | 1.9 | 1034 | 825 | −1.5 |
| IGF3 | 954 | 311 | 1.4 | 279 | 177 | −2.6 | 1934 | 972 | 1.2 |
| No booster | 668 | 246 | | 723 | 525 | | 1666 | 371 | |

| | gsdf | | | inhα | | | amh | | |
|---|---|---|---|---|---|---|---|---|---|
| males | mean | SD | F-c | mean | SD | F-c | mean | SD | F-c |
| Control | 7481 | 1463 | | 11199 | 2708 | | 18259 | 4885 | |
| GSDFb | 8781 | 798 | 1.2 | 5697 | 1140 | −2.0 | 9662 | 1971 | −1.9 |
| GSDFc | 5653 | 2596 | −1.3 | 5978 | 3177 | −1.9 | 7770 | 4988 | −2.3 |
| GDF9c | 7088 | 1651 | −1.1 | 6147 | 1467 | −1.8 | 8894 | 4405 | −2.1 |
| GDF9b | 6595 | 1718 | −1.1 | 5330 | 3274 | −2.1 | 12152 | 7528 | −1.5 |
| CD205bc | 5341 | 452 | −1.4 | 4979 | 3408 | −2.2 | 7508 | 3334 | −2.4 |
| IGF3 | 3342 | 2239 | −2.2 | 4320 | 2970 | −2.8 | 7691 | 10434 | −2.4 |
| No booster | 7207 | 1771 | | 12008 | 2504 | | 18664 | 3317 | |

| | tcrac | | | igkc | | | vasa | | |
|---|---|---|---|---|---|---|---|---|---|
| females | mean | SD | F-c | mean | SD | F-c | mean | SD | F-c |
| Control | 3208 | 1938 | | 1973 | 1674 | | 3334 | 1326 | |
| GSDFb | 5526 | 1985 | 1.7 | 1631 | 976 | −1.2 | 5711 | 1220 | 1.7 |
| GSDFc | 2966 | 1271 | −1.1 | 1111 | 1045 | −1.8 | 3427 | 1034 | 1.0 |
| GDF9c | 1965 | 1433 | −1.6 | 3234 | 1845 | 1.6 | 2797 | 923 | −1.2 |
| GDF9b | 1814 | 1436 | −1.8 | 2964 | 801 | 1.5 | 3204 | 541 | −1.0 |
| CD205bc | 1298 | 1079 | −2.5 | 1502 | 1338 | −1.3 | 1997 | 988 | −1.7 |
| IGF3 | 3624 | 1070 | 1.8 | 334 | 222 | 2.5 | 3426 | 897 | 1.9 |
| No booster | 2000 | 1753 | | 132 | 84 | | 1770 | 2294 | |

| | gsdf | | | inhα | | | amh | | |
|---|---|---|---|---|---|---|---|---|---|
| females | mean | SD | F-c | mean | SD | F-c | mean | SD | F-c |
| Control | 995 | 475 | | 2752 | 1698 | | 429 | 145 | |
| GSDFb | 794 | 222 | −1.3 | 5173 | 4165 | 1.9 | 518 | 84 | 1.2 |
| GSDFc | 607 | 410 | −1.6 | 1826 | 577 | −1.5 | 403 | 146 | −1.1 |
| GDF9c | 1880 | 248 | 1.9 | 1767 | 658 | −1.6 | 279 | 77 | −1.5 |
| GDF9b | 899 | 417 | −1.1 | 3511 | 1640 | 1.3 | 414 | 70 | −1.0 |
| CD205bc | 1324 | 166 | 1.3 | 887 | 217 | −3.1 | 210 | 62 | −2.0 |
| IGF3 | 986 | 243 | −2.0 | 2089 | 491 | −1.3 | 370 | 125 | −1.6 |
| No booster | 1938 | 1645 | | 2771 | 1908 | | 584 | 246 | |

Generally, expression of genes showed high variation within all variants; therefore, the differences in average expressions between groups, although frequently considerable, were not always significant. Nevertheless, the effect of treatment was clearly found in a number of variants, and certain pattern in gene expression related to developmental advancement and specific treatment was observed.

Differential Expression in Time:

In testes, expression of tcrac in all treatments was downregulated at 15 days post-treatment (dpt), but upregulated at 30 dpt, as compared to controls; it was opposite in the case of amh, where upregulation occurred at 15 dpt (with the exception of anti-CD205), followed by downregulation at 30 dpt. In ovaries, igkc expression showed an inverse relationship. Variants downregulated at 15 dpt (anti-GDF9), were upregulated at 30 dpt and variants upregulated at 15 dpt (anti-GSDF and anti-CD205) were downregulated at 30 dpt.

Differential Expression in Gonads:

Expression of tcrac in anti-GSDFc, anti-GDF9b, anti-GDF9c, and anti-CD205bc variants at 30 dpt was upregulated in testes but downregulated in ovaries. In anti-GSDFb treatment at 30 dpt, expression of vasa was downregulated in testes but significantly upregulated in ovaries. Similarly, expression of inhα was significantly downregulated in testes, but significantly upregulated in ovaries.

Expression of tcrac:

At 15 dpt, expression in testes and ovaries was downregulated in all treatments as compared to controls (except for ovary in anti-GSDFb treatment). At 30 dpt, expression in testes was upregulated in all treatments, contrary to ovary, where expression in 4 of 6 treatments was downregulated. Significant downregulation was found in ovaries: in anti-GDF9c (15 dpt) and anti-CD205bc (30 dpt) variants. Significant upregulation was observed in the anti-GSDFb variant (30 dpf).

Expression of igkc:

At 15 dpt, expression was generally upregulated in both testes and ovaries, with exception of anti-GDF9 treatments. At 30 dpt, upregulation was in all variants in testes, and in anti-GDF9 variants in ovaries. Significant upregulation was found at 15 dpt in ovaries (anti-CD205bc treatment) and in anti-GDF9 treatments in testes at 30 dpt.

Expression of vasa:

At 15 dpt, vasa was downregulated in all variants except for anti-GSDFb in ovary. At 30 dpt, there was upregulation in some variants. Significant downregulation was observed in ovaries (anti-GDF9c at 15 dpt and anti-CD205bc at 30 dpt). Significant upregulation was found in anti-GSDFb treatment in ovary at 30 dpt.

Expression of gsdf:

Varying expression according to treatment and tissue was observed, with rather low variation from the control values. Significant upregulation was observed at 30 dpt, in anti-GDF9c treated ovaries.

Expression of inhα:

At 15 dpt, upregulation of anti-GSDF variants and downregulation in anti-GDF9c was constant in both testes and ovaries. Significant downregulation in ovary in anti-GDF9c treatment was found. At 30 dpt, significant downregulation in all treatments in testes was found; also there was downregulation in 4 of 6 treatments in ovaries, but this was only significant in anti-CD205bc.

Expression of amh:

At 15 dpt, varying expression, mostly upregulation, was found in both tissues. At 30 dpt, amh was downregulated in all treatments in both tissues except for anti-GSDFb in ovary. In testes all but anti-GDF9b treatments resulted in significant downregulation. In ovaries, significant downregulation was observed in anti-GDF9c and anti-CD205bc treatments.

Treatment Efficiency at 15 dpt:

There was no significant effect found in male gonads, and this resulted in high variation in gene expression; nevertheless, some of the treatments resulted in several-fold change in gene expression as compared to controls, such as anti-GDF9b (2.5 and 3.6 fold downregulation of tcrac and igkc, respectively), and anti-CD205bc (2.8-fold upregulation of igkc and 3.8-fold downregulation of vasa). In ovary at 15 dpt, anti-GDF9c showed significant effect on expression of 3 out of 6 genes (downregulation of tcrac, vasa, and inhα).

Treatment Efficiency at 30 dpt:

The effect was more obvious than in 15 dpt samples. All variants (except anti-IGF3 and some control fish) received a booster injection at 15 dpt. Comparison on controls receiving booster with those not receiving booster, showed that booster injection significantly affected only igkc expression, elevating it 5.6 times. For this reason, gene expression in anti-IGF3 treatment was compared to non-boosted controls only.

In testes, all treatments resulted in downregulation in male-biased genes: gsdf, inhα, and amh (except gsdf expression in anti-GSDFb treatment), and upregulation in immune-related genes: tcrac and igkc (except igkc expression in the anti-IGF3 treatment). In ovaries, the pattern was more variable. The anti-CD205bc treatment resulted in significant downregulation of inhα and amh in both testes and ovaries, and tcrac and vasa in ovaries. Anti-GDF9c resulted in significant downregulation of inhα and amh, and upregulation of igkc in testes, whereas in ovaries, amh was significantly downregulated and gsdf significantly upregulated in this variant. Anti-GDF9b and anti-GSDFc showed significant effects in testes only (igkc upregulated and inhα downregulated in anti-GDF9b treatment, and inhα and amh downregulated in anti-GSDFc treatment). Anti-GSDFb resulted in significant downregulation of inhα and amh in testes, and significant upregulation of tcrac, vasa, and inhα in ovaries. Anti-IGF3 treatment resulted in significant downregulation in inhα, and amh) and igkc in testes.

Histological Examination of Juvenile Zebrafish Gonadal Tissue:

Examination of both testis and ovary of tg(vas::egfp) strain fish showed strong GFP expression in germ cells (FIGS. 2 and 3). In ovaries, expression was found throughout oocyte cytoplasm in all stages examined (stage IB, FIG. 2A; stages IA, II, and III, data not shown). In testis, expression was strong and transient in spermatogonia; however, expression was strikingly weaker in spermatocytes (FIG. 2B).

When comparing gonad morphology between control and treatment fish some histopathological effects of treatments were seen in both ovarian and testicular tissues. Those effects were generally related to organization of the early ovary, zona radiata development, atresia and atrophy in ovaries, inflammation in both testes and ovaries, and retardation of development in testes.

In control fish, the general morphology of a zebrafish ovary during the primary growth phase showed larger, further developed primary oocytes (Poc2) in the center of the ovary, whereas smaller (Poc1) primary oocytes were developing on the periphery (FIG. 3A,B). Ovaries maintained a uniform distribution of oocytes. This pattern was observed in all control fish sampled at 15 day post treatment (representative in FIG. 3B, n=7). In contrast, zebrafish from the anti-CD205 group at 15 days post treatment often had primary oocytes of various stages mixed throughout the ovary (effect visualized in 3 of 4 sampled fish; representative in FIG. 3C). In the remaining treatment groups examined on gonadal morphology using GFP signal, this effect was not apparent in anti-IGF3 and anti-GDF9b treatments; other treatments were not examined.

In 30 day post treatment, atresia and atrophy in previtellogenic (stages II, III) and vitellogenic (stage IV) oocytes were observed in anti-CD205 and anti-GSDFb treated fish. Also, thinner zona radiata on stage III oocytes, as compared to controls, was observed in anti-CD205 treated fish (FIG. 4). No apparent manifestations were observed in the remaining variants.

Inflammation, manifested in infiltration of peritoneal cells into gonads, frequently along with infiltration of eosinophilic granulocytes, possibly indicating granulomatous inflammation, was observed in several treatments, mostly anti-CD205 (FIG. 5). In ovaries, infiltration of eosinophilic granulocytes was associated with atretic and atrophic processes (e.g. FIG. 5C).

In testis, treatment effects were manifested by retarded development (FIG. 6). In several treatments, mostly anti-GDF9b and anti-GSDFb and c, testes of some relatively large male fish (over 23 mm total length) remained in the early stages of differentiation, whereas control males of this size had normally testes in spermatid stage or even producing spermatozoa. This effect was not observed in anti-CD205 and anti-GDF9c treated males.

Immunohistochemistry Examination of Juvenile Zebrafish Gonadal Tissue:

Examination of the ovary of tg(vas::egfp) strain fish in both control and 30 dpt anti-CD205 fish showed the presence of Bik signal (FIG. 7). In ovaries of control fish (FIG. 7A), the stage Ib oocytes and follicular cells showed poor expression of the Bik protein. In contrast, signal in both stage Ib oocytes and follicular cells of the treated fish was considerably stronger (FIG. 7 B,C,D). In addition to the strength of epifluorescence signal, the observed features in the anti-CD205 treated ovaries included presence of the signal inside the oocytes, with condensation of the signal around oocyte nucleus, clearly visible as a ring in many of the cells. This signal corresponded to the expected localization of Bik within the endoplasmic reticulum surrounding the nucleus. Also, strong expression of the signal in follicular cells surrounding oocytes was observed in the ovaries of treated fish.

Interpretation

The treatments against germ cell proteins (CD205 and IGF3) and supporting somatic cells proteins (GSDF and GDF9) showed variable effects, but generally they induced autoimmune response which, consequently, affected gonadal development. This can be concluded from:

Reduction of transcripts being markers of germ cells and supporting granulosa or Sertoli cells as the effect of treatment;

Retardation in weight, per analogiam to adult trial likely resulting from loss in gonadal weight;

Pathological features observed in gonadal morphology and histology;

Intensity of apoptotic processes occurring in both germ cells and somatic cells.

The effect was FSH-independent. FSH (follicle stimulating hormone) is a major regulator of both ovarian and testicular development. FSH is involved in regulation of genes affecting early germ cell proliferation and differentiation in fish; these factors belong to major regulatory pathways, such as Igf pathway (for example, igf3), and Tgfβ pathway (for example, gsdf, amh and inhα). Also, FSH is suggested to stimulate Sertoli cells proliferation. FSH upregulates inhα expression and induces downregulation of amh expression in trout testis (Sambroni et al. (2013) J. Mol. Endocrinol., 50, 1-18). In our study, we have been observing mostly a synergistic effect of treatments on amh and inhα expression, suggesting different mechanism than FSH stimulation. There is evidence that the GSDF role in germ cell proliferation does not involve FSH regulatory pathway (Sambroni et al. (2013). In the present study, the treatment with anti-GSDF resulted in significant downregulation on amh and inhα in gonads at 30 dpf, which also supports the conclusion that the effect of treatments on gene expression was not gonadotropin-mediated. Consequently, disturbances of gonadal development must be the result of immunization against target proteins important in gonadal development and resulting immune response.

Because of soma-germ cell signalling cross-talk, immunization against germ cell targets affected somatic supporting cells, and vice versa. Sertoli and granulosa cells derive from a common progenitor cell type. Inhibin alpha functions as an endocrine hormone from the gonads to regulate FSH secretion in the pituitary. In zebrafish, inhα is predominantly expressed in somatic follicle cells, increasing along with folliculogenesis. Amh expression is not detected in somatic cells of germ cell-ablated gonad of medaka, which indicates that signalling from germ cells is necessary to sustain amh expression in soma. Therefore, significant downregulation in both ovaries and testes, observed in anti-CD205 and anti-GDF9 treatments, could result from disturbance of soma-germline cross-talk in the gonads, caused by the efficient treatment to germ cells.

Our results of anti-CD205 and anti-GDF9 (germ cell proteins) treatments suggest the following mechanism:

At 15 dpt, the effect of treatment on early differentiation stages of germ cells was manifested in elevation in igkc expression (B-cell marker), decrease in vasa expression (germ cell marker), showing direct effect on germ cell development via immunity mechanism (manifested in inflammatory reaction and associated pathology in gonads). The effect on supporting somatic cells (Sertoli and granulosa), manifested in expression of inhα and amh, was insignificant because the target proteins were related to germ cells.

At 30 dpt, long-lasting effect on germ cells (manifested by decrease in vasa expression, gonadal histopathology, intensive apoptosis, and progressing retardation in weight) resulted in disruption of signalling from germ cells to Sertoli and granulosa cells, thus affected development of Sertoli and granulosa cells (manifested in decrease in inhα and amh expression and intensive apoptosis).

Results on anti-GSDF and anti-IGF3 treatments against Sertoli and granulosa cell-produced signals suggest the following mechanism:

At 15 dpt, immunization (manifested in elevated levels of igkc transcripts) resulted in compensatory transcription of relevant transcripts (manifested by upregulation in Sertoli/granulosa relevant inhα and amh expression) and simultaneous retardation of gonadal development (manifested in histological retardation of testis development).

At 30 dpt, further autoimmune reaction (manifested in elevated igkc expression) resulted in decomposition of Sertoli cells (manifested in decrease of inhα and amh expression), whereas less effect was observed on granulosa cells.

In conclusion, results of several analyses indicate that the vaccination against chosen target proteins of germ cells and supporting somatic cells in juvenile zebrafish gonad induces an immune reaction which, as a consequence, leads to a disturbance in the gonadal development. Induced immune reactions can be concluded from: elevated expression of immune genes (both B-cell and T-cell related); pathological features observed in gonadal histology (granulomastous-like inflammatory reaction); and immunohictochemistry (strong expression of a pro-apoptotic protein). Disturbance in gonadal development can be concluded from: decrease in expression of genes which are markers or are predominantly expressed in germ cells and in supporting somatic cells in a gonad; histopathological features including atresia, atrophy, abnormal cell distribution, and retardation of development; retardation in weight. Together, the results show that the injected IAMs induced auto-immune reaction against gonadal cells, which affected gonadal development.

It is noteworthy that the IAMs used in the present Example showed efficiency in both male and female gonad, in terms of the induced immune reaction and disturbance of gonadal development.

The invention claimed is:

1. A method of inhibiting maturation of the gonads of both male and female juvenile fish which comprises:
administering to said juvenile fish an antigenic peptide, said antigenic peptide being a fragment of a target protein within the gonads or corresponding to a short antigenic region of said target protein, and causing an immune response against that target protein and thereby inhibiting maturation of the gonads,
wherein the target protein is lymphocyte antigen 75 (CD205/Ly75), insulin-like growth factor 3 (IGF3), growth differentiation factor 9 (GDF9), or gonadal soma-derived growth factor (GSDF), and
wherein said antigenic peptide inhibits the maturation of gonads in both males and females.

2. The method of claim 1, wherein the immune response comprises stimulation of B cells and/or T cells in said fish.

3. The method of claim 1, wherein the immune response comprises production of antibodies which are specific for the target protein and/or binding of T cells to the target protein.

4. The method of claim 1, wherein the antigenic peptide is 10 to 40 amino acids in length.

5. The method of claim 1, wherein the antigenic peptide is a heteroantigen.

6. The method of claim 1, wherein the antigenic peptide is coupled to a carrier protein.

7. The method of claim 1, wherein the juvenile fish is a farmed fish.

8. The method of claim 7, wherein the juvenile fish is Atlantic salmon (*Salmo salar*), rainbow trout (*Oncorhynchus mykiss*), Atlantic cod (*Gadus morhua*), or Atlantic halibut (*Hippoglossus hippoglossus*).

9. The method of claim 1, wherein the antigenic peptide comprises SEQ ID NO:5.

10. The method of claim 1, wherein the antigenic peptide comprises SEQ ID NO:6.

11. The method of claim 1, wherein the antigenic peptide comprises SEQ ID NO:7.

12. The method of claim 1, wherein the antigenic peptide comprises SEQ ID NO:8.

13. The method of claim 1, wherein the antigenic peptide comprises SEQ ID NO:9.

14. The method of claim 1, wherein the antigenic peptide comprises SEQ ID NO:10.

15. The method of claim 1, wherein the antigenic peptide comprises SEQ ID NO:11.

16. The method of claim 1, wherein the antigenic peptide comprises SEQ ID NO:12.

17. The method of claim 1, wherein the antigenic peptide comprises SEQ ID NO:13.

* * * * *